United States Patent
Zhou

(10) Patent No.: US 8,354,434 B2
(45) Date of Patent: Jan. 15, 2013

(54) CYCLOUREA COMPOUNDS AS CALCIUM CHANNEL BLOCKERS

(75) Inventor: Xiaoming Zhou, Plainsboro, NJ (US)

(73) Assignee: Purdue Pharma L.P., Stamford, CT (US)

( * ) Notice: Subject to any disclaimer, the term of this patent is extended or adjusted under 35 U.S.C. 154(b) by 955 days.

(21) Appl. No.: 12/223,392

(22) PCT Filed: Jan. 15, 2007

(86) PCT No.: PCT/EP2007/000303
§ 371 (c)(1),
(2), (4) Date: Dec. 9, 2008

(87) PCT Pub. No.: WO2007/085357
PCT Pub. Date: Aug. 2, 2007

(65) Prior Publication Data
US 2009/0176838 A1    Jul. 9, 2009

Related U.S. Application Data

(60) Provisional application No. 60/762,887, filed on Jan. 30, 2006.

(51) Int. Cl.
| A61K 31/454 | (2006.01) |
| A61K 31/4439 | (2006.01) |
| A61K 31/4184 | (2006.01) |
| A61K 31/4178 | (2006.01) |
| A61K 31/4166 | (2006.01) |
| C07D 401/06 | (2006.01) |
| C07D 401/04 | (2006.01) |
| C07D 403/06 | (2006.01) |
| C07D 235/02 | (2006.01) |
| C07D 233/34 | (2006.01) |

(52) U.S. Cl. ........ 514/338; 514/322; 514/387; 514/393; 514/326; 514/341; 548/306.4; 548/302.7; 548/314.7; 548/326.1; 548/316.4; 546/210; 546/273.7; 546/274.4

(58) Field of Classification Search .................. 514/387, 514/392, 338, 322, 393, 326, 341; 548/302.7, 548/306.4, 316.4, 314.7, 326.1; 546/210, 546/273.7, 274.4
See application file for complete search history.

(56) References Cited

U.S. PATENT DOCUMENTS

| 3,161,645 A | 12/1964 | Janssen et al. |
| 3,184,460 A | 5/1965 | Akkerman et al. |
| 3,196,157 A | 7/1965 | Janssel et al. |
| 3,318,900 A | 5/1967 | Janssen et al. |
| 3,910,930 A | 10/1975 | Janssen et al. |
| 4,329,353 A | 5/1982 | Stokbroekx et al. |
| 4,886,817 A | 12/1989 | Takeda et al. |
| 5,831,005 A | 11/1998 | Zuckerman et al. |
| 5,869,515 A | 2/1999 | Freyne et al. |
| 5,877,278 A | 3/1999 | Zuckermann et al. |
| 5,952,510 A | 9/1999 | Freyne et al. |
| 5,977,301 A | 11/1999 | Zuckerman et al. |
| 5,994,376 A | 11/1999 | Freyne et al. |
| 6,136,839 A | 10/2000 | Isakson et al. |
| 6,150,355 A | 11/2000 | Kumazawa et al. |
| 6,166,209 A | 12/2000 | Adam et al. |
| 6,258,825 B1 | 7/2001 | Ozaki et al. |
| 6,262,066 B1 | 7/2001 | Tulshian et al. |
| 6,403,805 B1 | 6/2002 | Freyne et al. |
| 6,410,561 B1 | 6/2002 | Shinkai et al. |
| 6,455,527 B2 | 9/2002 | Tulshian et al. |
| 6,492,553 B1 | 12/2002 | Hulme et al. |
| 6,716,846 B2 | 4/2004 | Tulshian et al. |
| 6,867,222 B2 | 3/2005 | Sun et al. |
| 7,456,198 B2 | 11/2008 | Kyle et al. |
| 7,678,809 B2 | 3/2010 | Kyle et al. |
| 2002/0068830 A1 | 6/2002 | Freyne et al. |
| 2002/0115612 A1 | 8/2002 | Zuckermann et al. |
| 2003/0069249 A1 | 4/2003 | Sun et al. |
| 2005/0043378 A1 | 2/2005 | Axe et al. |

FOREIGN PATENT DOCUMENTS

| DE | 24 00 094 A1 | 7/1974 |
| EP | 0 008 259 A1 | 2/1980 |
| EP | 0 092 391 A2 | 10/1983 |
| EP | 0 268 229 A2 | 5/1988 |
| EP | 0 921 125 A1 | 6/1999 |
| FR | 1 516 714 A | 2/1968 |

(Continued)

OTHER PUBLICATIONS

Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*

(Continued)

*Primary Examiner* — Joseph Kosack
*Assistant Examiner* — Matthew Coughlin
(74) *Attorney, Agent, or Firm* — Sterne, Kessler, Goldstein & Fox P.L.L.C.

(57) ABSTRACT

The invention relates to cyclourea compounds of Formula I: or a pharmaceutically acceptable salt or solvate thereof, wherein $R^1$-$R^3$ and Z are defined as set forth in the specification. The invention is also directed to the use of compounds of Formula I to treat, prevent or ameliorate a disorder responsive to the blockade of calcium channels, and particularly N-type calcium channels. Compounds of the present invention are especially useful for treating pain.

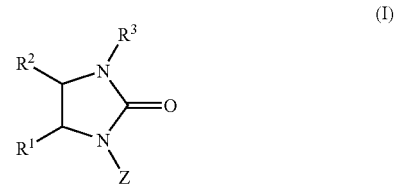

(I)

24 Claims, No Drawings

FOREIGN PATENT DOCUMENTS

| | | |
|---|---|---|
| WO | WO 97/10213 A1 | 3/1997 |
| WO | WO 97/14417 A1 | 4/1997 |
| WO | WO 97/40035 A1 | 10/1997 |
| WO | WO 98/54168 A1 | 12/1998 |
| WO | WO 99/29696 A1 | 6/1999 |
| WO | WO 99/36421 A1 | 7/1999 |
| WO | WO 99/48492 A1 | 9/1999 |
| WO | WO 99/50262 A1 | 10/1999 |
| WO | WO 99/59997 A1 | 11/1999 |
| WO | WO 00/06545 A1 | 2/2000 |
| WO | WO 01/41748 A2 | 6/2001 |
| WO | WO 03/042177 A1 | 5/2003 |
| WO | WO 03/089427 A1 | 10/2003 |
| WO | WO 2005/087747 A1 | 9/2005 |
| WO | WO 2006/023844 A2 | 3/2006 |
| WO | WO 2006/136561 A1 | 12/2006 |

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227).*

Supporting Information for Wang et al. J. Comb. Chem. 2004, 6, 899-902, pp. 1-6.*

Pasternak et al. Bioorg. Med. Chem. Lett. 1999, 9, 491-496.*

Brower, V., "New paths to pain relief," *Nat. Biotechnol.* 18:387-391, Nature America Inc. (2000).

Castellano, A., et al., "Cloning and Expression of a Neuronal Calcium Channel β Subunit," *J. Biol. Chem. 268:12359-12366*, The American Society for Biochemistry and Molecular Biology, Inc. (1993).

Chern, J.-H., et al., "Synthesis and antienteroviral activity of a series of novel, oxime ether-containing pyridyl imidazolidinones," *Bioorg. Med. Chem. Lett.* 14:5051-5056, Elsevier Ltd. (2004).

Clark, R.L. And Pessolano, A.A., "Synthesis of Some Substituted Benzimidazolones," *J. Am. Chem. Soc.* 80:1657-1662, Mack Printing Company (1958).

Davila, H.M., "Molecular and Functional Diversity of Voltage-Gated Calcium Channels," *Ann. NY Acad. Sci.* 868:102-117, The New York Academy of Sciences (1999).

Donati, D., et al., "A General Procedure for the Synthesis of Pyrido-Condensed Heterocycles," *Synthesis* No. 16:2518-2524, Georg Thieme Verlag (2003).

Dubel, S.J., et al., "Molecular cloning of the α-1 subunit of an ω-conotoxin-sensitive calcium channel," *Proc. Natl. Acad. Sci. U.S.A.* 89:5058-5062, The National Academy of Sciences of the United States of America (1992).

Filer, C.N., "Chapter 6: The Preparation and Characterization of Tritiated Neurochemicals," in *Isotopes in the Physical and Biomedical Sciences*, vol. 1, Labeled Compounds (Part A), Buncel, E. and Jones, J.R., eds., Elsevier, Amsterdam, BE, pp. 156-192 (1987).

Goff, D., et al., "The Synthesis of 2-Imidazolidones on Solid Support by Tandem Aminocylation / Michael Addition," *Tetrahedron Lett.* 39:1477-1480, Elsevier Science Ltd. (1998).

Gould, R.J., et al., "Antischizophrenic drugs of the diphenylbutylpiperidine type act as calcium channel antagonists," *Proc. Natl. Acad. Sci. USA 80:5122-5125*, The National Academy of Sciences of the United States of America (1983).

Hamill, O.P., et al., "Improved Patch-Clamp Techniques for High-Resolution Current Recording from Cells and Cell-Free Membrane Patches," *Pflügers Arch.* 391:85-100, Springer-Verlag (1981).

Hanson, G.R., "Chapter 72. Analgesic, Antipyretic and Anti-inflammatory Drugs," in Remington: *The Science and Practice of Pharmacy*, vol. II, Mack Printing Company, Easton, PA, pp. 1196-1221 (1995).

Hu, L-Y., et al., "Structure-Activity Relationship of N-Methyl-N-AralkylPeptidylamines as Novel N-Type Calcium Channel Blockers," *Bioorg. Med. Chem. Lett.* 9:2151-2156, Elsevier Science Ltd. (1999).

Hu, L-Y., et al., "Synthesis of a Series of 4-Benzyloxyaniline Analogues as Neuronal N-Type Calcium Channel Blockers with Improved Anticonvulsant and Analgesic Properties," *J. Med. Chem.* 42:4239-4249, American Chemical Society (1999).

Hu, L-Y., et al., "The Discovery of [1-(4-Dimethylamino-benzyl)-piperidin-4-yl]-[4-(3,3-dimethylbutyl)-phenyl]-(3-methyl-but-2-enyl)-Amine, an N-type $Ca^{+2}$ Channel Blocker with Oral Activity for analgesis," *Bioorg. Med. Chem* 8:1203-1212, Elsevier Science Ltd. (200).

Hunskaar, S., et al., "Formalin test in mice, a useful technique for evaluating mild analgesics," *J. Neurosci. Methods* 14:69-76, Elsevier Publishers B.V. (1985).

Insel, P.A., "Chapter 27. Analgesic-Antipyretic and Antiinflammatory Agents and Drugs Employed in the Treatment of Gout," in *Goodman & Gilman's The Pharmacological Basis of Therapeutics*, 9th Ed., Molinhoff, P.B. and Ruddon, R.W., eds., McGraw-Hill, New York, NY, pp. 617-657 (1996).

Ito, M., "Long-Term Depression," *Ann. Rev. Neurosci.* 12:85-102, Annual Reviews Inc. (1989).

Janis, R.J. And Triggle, D.J., "Chapter 13. Drugs Acting on Calcium Channels," in *Calcium Channels: Their Properties, Functions, Regulation and Clinical Relevance*, Hurwitz, L., et al., eds., CRC Press, London, England, pp. 195-249 (1991).

Kano, S., et al., "A Synthesis of Heterocyclic Fused Isoquinolines Through N-Acyliminium Ion Intermediates," *Synth. Commun.* 15:883-889, Marcel Dekker, Inc. (1985).

Kim, S.H. and Chung, J.M., "An experimental model for peripheral neuropathy produced by segmental spinal nerve ligation in the rat," *Pain 50:*355-363, Elsevier Science Publishers B.V. (1992).

Kim, H-L., et al., "Rat brain expresses an alternatively spliced form of the dihydropyridine-sensitive L-type calcium channel α2 subunit," *Proc. Natl. Acad. Sci. U.S.A.* 89:3251-3255, The National Academy of Sciences of the United States of America (1992).

Koch, W.J., et al., "cDNA Cloning of a Dihydropyridine-sensitive Calcium Channel from Rat Aorta. Evidence for the Existence of Alternatively Spliced Forms," *J. Biol. Chem.* 265:17786-17791, The American Society for Biochemistry and Molecular Biology, Inc. (1990).

Lam, P.Y.S., et al., "Copper-catalyzed general C-N and C-O bond cross-coupling with arylboronic acid," *Tetrahedron Letters* 42:3415-3418, Elsevier Science Ltd. (2001).

Levine, J. and Taiwo, Y., "Chapter 2. Inflammatory Pain," in *Textbook of Pain*, 3rd Ed., Wall, P.D. and Melzack, R., eds., Churchill Livingstone, Edinburgh, England, pp. 45-56 (1994).

Lin, Z., et al., "Identification of Functionally Distinct Isoforms of the N-Type $Ca^{2+}$Channel in Rat Sympathetic Ganglia and Brain," *Neuron 18:*153-166, Cell Press (1997).

Llopart, C.C., et al., "Lithiation of 1-arylimidazol-2(1H)-ones and 1-aryl-4,5-dihydroitnidazol-2-(1H)-ones," *Can. J Chem.* 82:1649-1661, NRC Canada (2004).

Lukyanetz, E.A., "Selective Blockade of N-Type Calcium Channels by Levetiracetam," *Epilepsia 43:*9-18, Blackwell Publishing (2002).

Nomoto, Y., et al., "Studies on Cardiotonic Agents. III. [1)] Synthesis of 1-[1-(6,7-Dimethoxy-4-quinazolinyl)-4-piperidinyl]-3-substituted 2-Imidazolidinone and 2-Imidazolidinethione Derivatives," *Chem. Pharm. Bull.* 38:2467-2471, Pharmaceutical Society of Japan (1990).

Nuglisch, J., et al., "Protective Effect of Nimodipine Against Ischemic Neuronal Damage in Rat Hippocampus Without Changing Postischemic Cerebral Blood Flow," *J. Cereb. Blood Flow Metab.* 10:654-659, Raven Press Ltd., New York (1990).

Matoba, K., et al., "Synthesis in the Diazasteroid Group. XIV. Synthesis of the 13,15-Diazasteroid System," *Chem. Pharm. Bull.* 28:1810-1813, The Pharmaceutical Society of Japan (1980).

Pragnell, M., et al., "Cloning and tissue-specific expression of the brain calcium channel β-subunit," *FEBS Lett.* 291:253-258, Elsevier Science Publishers B.V. (1991).

Raju, B., et al., "Solution-Phase Parallel Synthesis of Substituted Benzimidazoles," *J. Comb. Chem.* 4:320-328, American Chemical Society (2002).

Schwartz, A., et al., "Receptors for Calcium Antagonists," *Am. J. Cardiol.* 62:3G-6G, Excerpta Medica (1988).

Shia, K.-S., et al., "Design, Synthesis, and Structure-Activity Relationship of Pyridyl Imidazolidinones: A Novel Class of Potent and Selective Human Enterovirus 71 Inhibitors," *J. Med. Chem.* 45:1644-1655, American Chemical Society (2002).

Solomon, V.R., et al., "Design and synthesis and new antimalarial agents from 4-aminoquinoline," *Bioorg. Med. Chem.* 13:2157-2165, Elsevier Ltd. (Jan. 2005).

Song, Y., et al., "(S)-4-Methyl-2-(methylamino)pentanoic Acid [4,4-Bis(4-fluorophenyl)butyl]amide Hydrochloride, a Novel Calcium Channel Antagonist, Is Efficacious in Several Animal Models of Pain," *J. Med. Chem.* 43:3474-3477, American Chemical Society (2000).

Stein, C., et al., "Unilateral Inflammation of the Hindpaw in Rats as a Model of Prolonged Noxious Stimulation: Alterations in Behavior and Nociceptive Thresholds," *Pharmacol. Biochem. Behavior.* 31:445-451, Pergamon Press plc (1988).

Tapia, I., et al., "2,3-Dihydro-2-oxo-1H-benzimidazole-1-carboxamides with Selective Affinity for the 5-HT$_4$ Receptor: Synthesis and Structure-Affinity and Structure-Activity Relationships of a New Series of Partial Agonist and Antagonist Derivatives," *J. Med. Chem. 43:*2870-2880, American Chemical Society (1999).

Vanegas, H. and Schaible, H-G., "Effects of antagonists to high-threshold calcium channels upon spinal mechanisms of pain, hyperalgesia and allodynia," *Pain* 85:9-18, Elsevier Science B.V. (2000).

Wallace, M.S., "Calcium and Sodium Channel Antagonists for the Treatment of Pain," *Clin. J. Pain* 16:S80-S85, Lippincott Williams & Wilkins, Inc. (2000).

Wang, C.-C. and Li, W.-R., "Traceless Solid-Phase Synthesis of Substituted Benzimidazolones," J. Comb. Chem. 6:899-902, American Chemical Society (2004).

International Search Report for International Application No. PCT/EP2007/000303, European Patent Office, Netherlands, mailed on Mar. 29, 2007.

Obase, H., et al., "New Antihypertensive Agents, I. synthesis and Antihypertensive Activity of Some 4-Piperidylbenzimidazolinone Derivatives" *Chem. Pharm. Bull.* 30:462-473, Japan (1982).

Database HCAPLUS on STN, Chemical Accession No. 1998:650062 (Document No. 129-290436), English language abstract of Kyle, D., et al., "Psuedo- and non-peptide bradykinin receptor antagonists," Cont.-in-part of U.S. Ser. No. 353, 426, Scios Inc., USA (1998) 3 pages.

Database HCAPLUS on STN, Chemical Accession No. 1998:795002 (Document No. 130:52418), english language abstract of Ozaki, S., et al., "Preparation of 2-oxoimidazole derivatives as pharmaceuticals," PCT Int. Appl., Banyu Pharmaceutical Co., Ltd., Japan (1998), 5 pages.

Database HCAPLUS on STN, Chemical Accession No. 1998:644540 (Document No. 130:47501), English language abstract of Taylor, F. and Dickenson, A., "Nociceptin/orphanin FQ. A new opioid, a new analgesic?" *NeuroReport 9*:R65-R70, Lippincott, William & Wilkins, UK (1998), 3 pages.

Unverified English language abstract of European Patent Application No. EP0008259 A1, Duhault, J., et al., espacenet, European Patent Office, France (1980).

Office action mailed on Feb. 27, 2007 in U.S. Appl. No. 09/730,934, Kyle, et al., filed Dec. 6, 2000.

Office action mailed on Jan. 23, 2008 in U.S. Appl. No. 09/730,934, Kyle, et al., filed Dec. 6, 2000.

Office action mailed on Mar. 27, 2009 in U.S. Appl. No. 11/494,826, Kyle, et al., filed Jul. 28, 2006.

Dastabase USPATFULL on STN International, Access No. 2001:107907, "2-Oxoimidazole Derivatives," Ozaki, S., et al., U.S. Patent No. 6,258,825, 107 pages, 2001.

* cited by examiner

SEQUENCE LISTING

<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer

<400> SEQUENCE: 1
caccatggtc cgcttcgggg ac                                          22

<210> SEQ ID NO 2
<211> LENGTH: 19
<212> TYPE: DNA
<213> ORGANISM: Artificial Sequence
<220> FEATURE:
<223> OTHER INFORMATION: Synthetic Primer

<400> SEQUENCE: 2
ccgttcagtg gcctcctcc                                              19

<210> SEQ ID NO 3
<211> LENGTH: 23
<212> TYPE: DNA
<213> ORGANISM: Artificial Sequence
<220> FEATURE:
<223> OTHER INFORMATION: Synthetic Primer

<400> SEQUENCE: 3
ctagcaccag tgatcctggt ctg                                         23

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

```
<400> SEQUENCE: 4
agtgcgttgt gagcgcagta                                                    20

<210> SEQ ID NO 5
<211> LENGTH: 21
<212> TYPE: DNA
<213> ORGANISM: Artificial Sequence
<220> FEATURE:
<223> OTHER INFORMATION: Synthetic Primer

<400> SEQUENCE: 5
caccatggtc cagaagagcg g                                                  21

<210> SEQ ID NO 6
<211> LENGTH: 21
<212> TYPE: DNA
<213> ORGANISM: Artificial Sequence
<220> FEATURE:
<223> OTHER INFORMATION: Synthetic Primer

<400> SEQUENCE: 6
tctcagcgga tgtagacgcc t                                                  21

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer

<400> SEQUENCE: 7
caccatgtat gacgactcct ac                                                 22

<210> SEQ ID NO 8
<211> LENGTH: 23
<212> TYPE: DNA
<213> ORGANISM: Artificial Sequence
<220> FEATURE:
<223> OTHER INFORMATION: Synthetic Primer

<400> SEQUENCE: 8
ggtggtcagt agctgtcctt agg                                                23

<210> SEQ ID NO 9
<211> LENGTH: 21
<212> TYPE: DNA
<213> ORGANISM: Artificial Sequence
<220> FEATURE:
<223> OTHER INFORMATION: Synthetic Primer

<400> SEQUENCE: 9
caccatggct gctggctgcc t                                                  21

<210> SEQ ID NO 10
<211> LENGTH: 25
<212> TYPE: DNA
<213> ORGANISM: Artificial Sequence
<220> FEATURE:
<223> OTHER INFORMATION: Synthetic Primer

<400> SEQUENCE: 10
agagggtcac catagatagt gtctg                                              25

<210> SEQ ID NO 11
<211> LENGTH: 22
```

```
<212> TYPE: DNA
<213> ORGANISM: Artificial Sequence
<220> FEATURE:
<223> OTHER INFORMATION: Synthetic Primer

<400> SEQUENCE: 11
caccatgatt cgggccttcg ct                                          22

<210> SEQ ID NO 12
<211> LENGTH: 25
<212> TYPE: DNA
<213> ORGANISM: Artificial Sequence
<220> FEATURE:
<223> OTHER INFORMATION: Synthetic Primer

<400> SEQUENCE: 12
agcctgcgga ctacaggttg ctgac                                       25
```

CYCLOUREA COMPOUNDS AS CALCIUM CHANNEL BLOCKERS

This application is a National Stage of International Application No. PCT/EP2007/000303, filed Jan. 15, 2007, which claims the benefit of U.S. Provisional Application No. 60/762,887, filed Jan. 30, 2006. The entirety of each of these applications is incorporated by reference herein.

BACKGROUND OF THE INVENTION

1. Field of the Invention

This invention is in the field of medicinal chemistry. The invention relates to novel cyclourea compounds and the use of these compounds as blockers of calcium ($Ca^{2+}$) channels.

2. Background Art

Calcium ions play fundamental roles in the regulation of many cellular processes. It is therefore essential that their intracellular levels be maintained under strict, yet dynamic control (Davila, H. M., *Annals of the New York Academy of Sciences*, pp. 102-117 (1999)). Voltage-gated calcium channels (VGCC) serve as one of the important mechanisms for fast calcium influx into the cell. Calcium channels are hetero-oligomeric proteins consisting of a pore-forming subunit ($\alpha 1$), which is able to form functional channels on its own in heterologous expression systems, and a set of auxiliary or regulatory subunits. Calcium channels have been classified based on their pharmacological and/or electrophysiological properties. The classification of voltage-gated calcium channels divides them into three groups: (i) high voltage-activated (HVA) channels, which include L-, N-, P-, and Q-types; (ii) intermediate (IVA) voltage-activated R-type channels; and (iii) low voltage-activated (LVA) T-type channels (Davila, supra). Voltage-gated calcium channels (VGCC) are also known as voltage-dependent calcium channels (VDCC) or voltage-sensitive calcium channels (VSCC).

Voltage-sensitive calcium channels (VSCC) regulate intracellular calcium concentration, which affects various important neuronal functions such as cellular excitability, neurotransmitter release, hormone secretion, intracellular metabolism, neurosecretory activity and gene expression (Hu et al., *Bioorganic & Medicinal Chemistry* 8:1203-1212 (2000)). N-type channels are found mainly in central and peripheral neurons, being primarily located on presynaptic nerve terminals. These channels regulate the calcium flux required for depolarization-evoked release of a transmitter from synaptic endings. The transmission of pain signals from the periphery to the central nervous system (CNS) is mediated by N-type calcium channels located in the spinal cord (Song et al., *J. Med. Chem.* 43:3474-3477 (2000)).

The six types of calcium channels (i.e., L, N, P, Q, R, and T) are expressed throughout the nervous system (Wallace, M. S., *The Clinical Journal of Pain* 16:580-585 (2000)). Voltage-sensitive calcium channels of the N-type exist in the superficial laminae of the dorsal horn and are thought to modulate nociceptive processing by a central mechanism. Blockade of the N-type calcium channel in the superficial dorsal horn modulates membrane excitability and inhibits neurotransmitter release, resulting in pain relief. Wallace (supra) suggests that based on animal models, N-type calcium channel antagonists have a greater analgesic potency than sodium channel antagonists.

N-type calcium channel blockers have usefulness for neuroprotection and analgesia. Ziconotide, which is a selective N-type calcium channel blocker, has been found to have analgesic activity in animal models and neuroprotective activity in focal and global ischemia models (Song et al., supra). Examples of known calcium channel blockers include flunarizine, fluspirilene, cilnipide, PD 157767, SB-201823, SB-206284, NNC09-0026, and PD 151307 (Hu et al., supra).

Blockade of N-type channels can prevent and/or attenuate subjective pain as well as primary and/or secondary hyperalgesia and allodynia in a variety of experimental and clinical conditions (Vanegas, H. et al., *Pain* 85:9-18 (2000)). N-type voltage-gated calcium channels (VGCC) play a major role in the release of synaptic mediators such as glutamate, acetylcholine, dopamine, norepinephrine, gamma-aminobutyric acid (GABA) and calcitonin gene-related peptide (CGRP).

Inhibition of voltage-gated L-type calcium channels has been shown to be beneficial for neuroprotection (Song et al., supra). However, inhibition of cardiac L-type calcium channels can lead to hypotension. It is believed that a rapid and profound lowering of arterial pressure tends to counteract the neuroprotective effects of L-type calcium channel blockers. A need exists for antagonists that are selective for N-type calcium channels over L-type calcium channels to avoid potential hypotensive effects.

U.S. Pat. No. 3,184,460 to Akkerman et al. describes 1-(alkoxyphenylalkyl)-2-imidazolidinones that act on the central nervous system.

Matoba et al. (*Chem. Pharm. Bull.* 28(6):1810-1813 (1980)) describe 1-[2-(3,4-dimethoxyphenyl)ethyl]imidazolidin-2-one, 1,3-bis[2-(3,4-dimethoxyphenyl)ethyl]imidazolidin-2-one, 1-(2-phenylethyl)imidazolidin-2-one, and 1,3-bis(2-phenylethyl)imidazolidin-2-one as intermediates.

U.S. Pat. No. 6,403,805 to Freyne et al. describes 1,3-dihydro-1-(phenylalkyl)-2H-imidazol-2-one derivatives having phosphodiesterase IV (PDE IV) and cytokine inhibiting activity.

U.S. Patent Application Publication No. 2003/0069249 by Sun et al. describes 1,3-dihydro-2H-benzimidazol-2-one derivatives that exhibit affinity to the ORL1 receptor.

Wang et al. (*Journal of Combinatorial Chemistry* 6:899-902 (2004)) describe a solid phase synthesis of substituted benzimidazolones.

BRIEF SUMMARY OF THE INVENTION

The present invention is related to the use of compounds represented by Formula I, below, as blockers of calcium ($Ca^{2+}$) channels. Certain compounds of Formula I show selectivity as N-type calcium channel blockers.

The invention is also related to treating, preventing or ameliorating a disorder responsive to the blockade of calcium channels in a mammal suffering from excess activity of said channels by administering an effective amount of a compound of Formula I as described herein. Specifically, the invention is related to treating, preventing or ameliorating a disorder responsive to the blockade of N-type calcium channels in a mammal suffering from excess activity of said channels by administering an effective amount of a compound of Formula I as described herein.

A number of compounds useful in the present invention have not been heretofore reported. Thus, one aspect of the present invention is directed to novel compounds of Formula I.

Another aspect of the present invention is directed to the use of the novel compounds of Formula I as blockers of N-type calcium channels.

A further aspect of the present invention is to provide a method for treating, preventing or ameliorating stroke, head trauma, epilepsy, pain (e.g., acute pain or chronic pain, which includes, but is not limited to, neuropathic pain and inflammatory pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia, by administering an effective amount of a compound of Formula I to a mammal in need of such treatment, prevention or amelioration.

A further aspect of the present invention is to provide a pharmaceutical composition useful for treating, preventing or ameliorating a disorder responsive to the blockade of calcium ion channels, especially N-type calcium ion channels, said pharmaceutical composition containing an effective amount of a compound of Formula I in a mixture with one or more pharmaceutically acceptable carriers.

Also, an aspect of the present invention is to provide a method of modulating calcium channels, especially N-type calcium channels, in a mammal, wherein said method comprises administering to the mammal an effective amount of at least one compound of Formula I.

A further aspect of the present invention is to provide $^3H$ or $^{14}C$ radiolabeled compounds of Formula I and their use as radioligands for their binding site on the calcium channel.

A further aspect of the invention is to provide a method for screening a candidate compound for the ability to bind to a receptor using a $^3H$ or $^{14}C$ radiolabeled compound of Formula I. This method comprises a) introducing a fixed concentration of the radiolabeled compound to the receptor to form a mixture; b) titrating the mixture with a candidate compound; and c) determining the binding of the candidate compound.

A further aspect of the invention is to provide the use of a compound of Formula I for the manufacture of a medicament for treating, preventing or ameliorating stroke, head trauma, epilepsy, pain, migraine, a mood disorder, schizophrenia, a neurodegenerative disorder, depression, anxiety, a psychosis, hypertension, or cardiac arrhythmia in a mammal. In a preferred embodiment, the invention provides the use of a compound of Formula I for the manufacture of a medicament for treating, preventing or ameliorating acute pain, chronic pain, or surgical pain.

Additional embodiments and advantages of the invention will be set forth in part in the description that follows, and will flow from the description, or may be learned by practice of the invention. The embodiments and advantages of the invention will be realized and attained by means of the elements and combinations particularly pointed out in the appended claims.

It is to be understood that both the foregoing summary and the following detailed description are exemplary and explanatory only and are not restrictive of the invention, as claimed.

DETAILED DESCRIPTION OF THE INVENTION

One aspect of the present invention is based on the discovery that compounds of Formula I act as blockers of $Ca^{2+}$ channels. In view of this discovery, compounds of Formula I are seen as useful for treating disorders responsive to the blockade of calcium ion channels. In one aspect, it has been found that certain compounds of Formula I selectively block N-type calcium ion channels and, thus, are useful for treating disorders responsive to the selective blockade of N-type calcium ion channels.

The compounds useful in this aspect of the invention are compounds represented by Formula I:

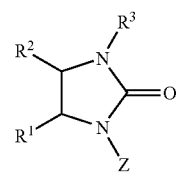

or a pharmaceutically acceptable salt, prodrug or solvate thereof, wherein:

Z is selected from the group consisting of $Z^1$ and $Z^2$, wherein

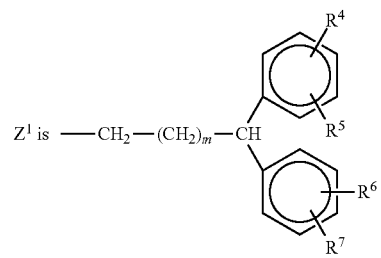

and $Z^2$ is $-CH_2-(CH_2)_n-R^8$;

$R^1$ and $R^2$ are both hydrogen or $R^1$ and $R^2$, together with the carbon atoms to which they are attached, form a fused cyclopropyl ring or a fused phenyl ring;

$R^3$ is selected from the group consisting of
(i) hydrogen;
(ii) alkyl;
(iii) $C_{3-6}$ cycloalkyl;
(iv) $-(CH_2)_p-Y$;

(v)

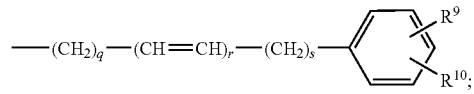

(vi)

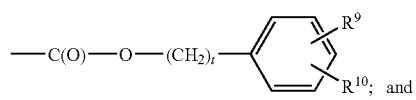

(vii)

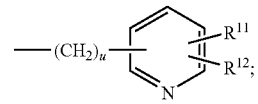

$R^4$, $R^5$, $R^6$, and $R^7$ are each independently selected from the group consisting of hydrogen, alkyl, alkoxy, halogen, haloalkyl, haloalkoxy, hydroxy, hydroxyalkyl, cyano, amino, aminoalkyl, alkylamino, and dialkylamino;

$R^8$ is selected from the group consisting of
phenyl optionally substituted with one, two or three substituents independently selected from the group consisting of alkyl, alkoxy, halogen, haloalkyl, haloalkoxy, hydroxy, hydroxyalkyl, cyano, amino, aminoalkyl, alkylamino, and dialkylamino;

pyridyl optionally substituted with one or two substituents independently selected from the group consisting of alkyl, halogen, haloalkyl, haloalkoxy, and alkoxy;

thiazolyl optionally substituted with one or two substituents independently selected from the group consisting of alkyl, alkoxy, halogen, and haloalkyl;

$R^9$ and $R^{10}$ are each independently selected from the group consisting of hydrogen, halogen, alkyl, alkoxy, haloalkyl, haloalkoxy, cyano, hydroxy, and hydroxyalkyl;

$R^{11}$ and $R^{12}$ are each independently selected from the group consisting of hydrogen, halogen, alkyl, alkoxy, haloalkyl, haloalkoxy, cyano, hydroxy, and hydroxyalkyl;

Y is a 3-7 membered saturated heterocyclic ring optionally substituted with one or two substituents independently selected from the group consisting of alkyl, alkoxy, halogen, haloalkyl, haloalkoxy, cyano, hydroxy, and hydroxyalkyl;

m is 0, 1, 2, 3, 4, or 5;

n is 0, 1, or 2;

p is 0, 1, 2, 3, or 4;

q and s are independently 0, 1, 2, 3, 4, or 5;

r is 0 or 1;

t is 0, 1, 2, 3, or 4; and u is 0, 1, 2, 3, or 4.

The groups $R^4$-$R^7$ and $R^9$-$R^{12}$, when themselves not equal to H, each take place of a hydrogen atom that would otherwise be present in any position on the aryl or heteroaryl ring to which the R group is attached. Similarly, the optional substituents attached to the phenyl, pyridyl and thiazolyl rings as defined for $R^8$ each take the place of a hydrogen atom that would otherwise be present in any position on the aryl or heteroaryl rings.

One group of compounds useful in this aspect of the present invention are compounds of Formula I where $R^1$-$R^{12}$, Z, Y, m, n, p, q, r, s, t, and u are as described above, with the provisos that 1) when $R^1$ and $R^2$ are both hydrogen, Z is $Z^2$, and $R^3$ is (i) or (v), where r is 0 and $R^9$ and $R^{10}$ are each independently hydrogen or alkoxy, then $R^8$ is not phenyl or 3,4-dimethoxyphenyl; or 2) when $R^1$ and $R^2$ together form a fused phenyl ring, Z is $Z^2$, and $R^8$ is an unsubstituted phenyl group, then $R^3$ is not alkyl.

In one embodiment, compounds useful in the present invention are compounds represented by Formula II:

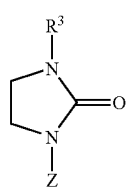

II or a pharmaceutically acceptable salt, prodrug, or solvate thereof, wherein $R^3$ and Z are as defined above for Formula I.

In a further embodiment, compounds useful in the present invention are compounds represented by Formula III:

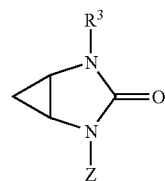

III or a pharmaceutically acceptable salt, prodrug, or solvate thereof, wherein $R^3$ and Z are as defined above for Formula I.

In a further embodiment, compounds useful in the present invention are compounds represented by Formula IV:

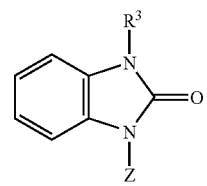

IV or a pharmaceutically acceptable salt, prodrug, or solvate thereof, wherein $R^3$ and Z are as defined above for Formula I.

In one embodiment, compounds useful in the present invention are compounds of Formulae I-IV, wherein Z is $Z^1$.

In another embodiment, compounds useful in the present invention are compounds of Formulae I-IV, wherein Z is $Z^2$.

A group of compounds useful in the present invention includes compounds of Formula I where $R^3$ is selected from the group consisting of (i) hydrogen, (ii) alkyl, and (iii) $C_{3-6}$ cycloalkyl; preferably selected from the group consisting of hydrogen, $C_{1-4}$ alkyl and $C_{3-6}$ cycloalkyl; more preferably selected from the group consisting of $C_{1-4}$ alkyl and $C_{3-6}$ cycloalkyl; and more preferably selected from the group consisting of methyl, ethyl, propyl, iso-propyl, butyl, tert-butyl, cyclopropyl, cyclobutyl, and cyclopentyl. Advantageously, $R^3$ is selected from the group consisting of methyl, ethyl, propyl, iso-propyl, tert-butyl, and cyclopropyl.

Another group of compounds useful in the present invention includes compounds of Formula I where $R^3$ is (iv) —$(CH_2)_p$—Y, wherein Y is a 3-7 membered saturated heterocyclic ring optionally substituted with one or two substituents independently selected from the group consisting of alkyl, alkoxy, halogen, haloalkyl, haloalkoxy, cyano, hydroxy, and hydroxyalkyl and p is 0, 1, 2, 3, or 4. Preferably, Y is a 3-6 membered saturated heterocyclic ring consisting of carbon atoms and one or two heteroatoms selected from the group consisting of O, N, and S, wherein the heterocyclic ring is optionally substituted with one or two substituents independently selected from the group consisting of alkyl, alkoxy, halogen, haloalkyl, haloalkoxy, cyano, hydroxy, and hydroxyalkyl; preferably independently selected from the group consisting of $C_{1-4}$ alkyl, $C_{1-4}$ alkoxy, halogen, halo($C_{1-3}$)alkyl, halo($C_{1-3}$)alkoxy, cyano, hydroxy, and hydroxy($C_{1-4}$)alkyl; and more preferably selected from the group consisting of hydrogen, methyl, ethyl, methoxy, ethoxy, fluoro, chloro, trifluoromethyl, trifluoroethyl, trifluoromethoxy, cyano, hydroxy, and hydroxymethyl. Useful compounds include those where the saturated heterocyclic ring is unsubstituted.

Advantageously, Y is a saturated heterocyclic ring having the formula

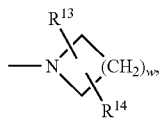

wherein $R^{13}$ and $R^{14}$ are each independently selected from the group consisting of hydrogen, alkyl, alkoxy, halogen, haloalkyl, haloalkoxy, cyano, hydroxy, and hydroxyalkyl, and w is 0, 1, 2, or 3. Preferably, $R^{13}$ and $R^{14}$ are each independently selected from the group consisting of hydrogen, $C_{1-4}$ alkyl, $C_{1-4}$ alkoxy, halogen, halo($C_{1-3}$)alkyl, halo($C_{1-3}$)alkoxy, cyano, hydroxy, and hydroxy($C_{1-4}$)alkyl; and more preferably hydrogen, methyl, ethyl, methoxy, ethoxy, fluoro, chloro, trifluoromethyl, trifluoroethyl, trifluoromethoxy, cyano, hydroxy, and hydroxymethyl. Advantageously, $R^{13}$ and $R^{14}$ are both hydrogen. Preferably, w is 2 or 3. Useful compounds of Formula I include those where Y is N-pyrrolidinyl or N-piperidinyl. Preferably, p is 0, 1, 2, or 3.

Another group of compounds useful in the present invention includes compounds of Formula I where $R^3$ is (v)

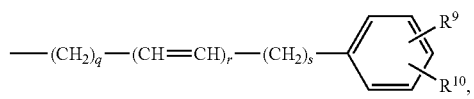

wherein $R^9$ and $R^{10}$ are each independently selected from the group consisting of hydrogen, halogen, alkyl, alkoxy, haloalkyl, haloalkoxy, cyano, hydroxy, and hydroxyalkyl, r is 0 or 1, and q and s are each independently 0, 1, 2, 3, 4, or 5. Preferably, $R^9$ and $R^{10}$ are each independently selected from the group consisting of hydrogen, $C_{1-4}$ alkyl, $C_{1-4}$ alkoxy, halogen, halo($C_{1-3}$)alkyl, halo($C_{1-3}$)alkoxy, cyano, hydroxy, and hydroxy($C_{1-4}$)alkyl; and more preferably each independently selected from the group consisting of hydrogen, methyl, ethyl, methoxy, ethoxy, fluoro, chloro, trifluoromethyl, trifluoroethyl, trifluoromethoxy, cyano, hydroxy, and hydroxymethyl. Useful compounds include those where $R^9$ and $R^{10}$ are both hydrogen. A useful group of compounds includes those where q and r are both 0 and s is 0, 1, 2, 3, or 4; and preferably s is 0, 1, 2, or 3. Another useful group of compounds includes those where q is 1 or 2, r is 1, and s is 0, 1, 2, or 3; and preferably s is 0, 1 or 2.

Another group of compounds useful in the present invention includes compounds of Formula I where $R^3$ is (vi)

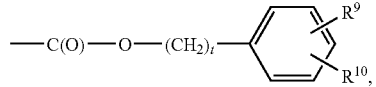

wherein $R^9$ and $R^{10}$ are each independently selected from the group consisting of hydrogen, halogen, alkyl, alkoxy, haloalkyl, haloalkoxy, cyano, hydroxy, and hydroxyalkyl, and t is 0, 1, 2, 3, or 4. Preferably, t is 0, 1, or 2.

Another group of compounds useful in the present invention includes compounds of Formula I where $R^3$ is (vii)

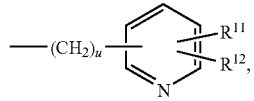

wherein $R^{11}$ and $R^{12}$ are each independently selected from the group consisting of hydrogen, halogen, alkyl, alkoxy, haloalkyl, haloalkoxy, cyano, hydroxy, and hydroxyalkyl, and u is 0, 1, 2, 3 or 4. Preferably, $R^{11}$ and $R^{12}$ are each independently selected from the group consisting of hydrogen, $C_{1-4}$ alkyl, $C_{1-4}$ alkoxy, halogen, halo($C_{1-3}$)alkyl, halo($C_{1-3}$)alkoxy, cyano, hydroxy, and hydroxy($C_{1-4}$)alkyl; and more preferably each is independently selected from the group consisting of hydrogen, methyl, ethyl, methoxy, ethoxy, fluoro, chloro, trifluoromethyl, trifluoroethyl, trifluoromethoxy, cyano, hydroxy, and hydroxymethyl. Useful compounds include those where $R^{11}$ and $R^{12}$ are independently selected from the group consisting of hydrogen, alkyl, and halogen. Advantageously, $R^{11}$ and $R^{12}$ are both hydrogen. Preferably, u is 0, 1, 2, or 3, and more preferably 0, 1, or 2. The —($CH_2$)$_u$— group is attached to the 2-, 3-, or 4-position of the pyridyl ring.

Preferably, $R^4$, $R^5$, $R^6$ and $R^7$ are each independently selected from the group consisting of hydrogen, alkyl, alkoxy, halogen, haloalkyl, haloalkoxy, hydroxy, cyano, amino, alkylamino, and dialkylamino. More preferably, $R^4$, $R^5$, $R^6$ and $R^7$ are each independently selected from the group consisting of hydrogen, $C_{1-6}$ alkyl, $C_{1-6}$ alkoxy, halogen, halo($C_{1-6}$)alkyl, halo($C_{1-6}$)alkoxy, hydroxy, cyano, amino, ($C_{1-6}$)alkylamino and di($C_{1-6}$) alkylamino; and more preferably independently selected from the group consisting of hydrogen, $C_{1-4}$ alkyl, $C_{1-4}$ alkoxy, halogen, halo($C_{1-3}$)alkyl, halo($C_{1-3}$)alkoxy, hydroxy, cyano, amino, and di($C_{1-3}$)alkylamino. Advantageously, $R^4$, $R^5$, $R^6$ and $R^7$ are each independently selected from the group consisting of hydrogen, methyl, ethyl, propyl, isopropyl, methoxy, ethoxy, halogen (especially fluorine), trifluoromethyl, trifluoromethoxy, hydroxy, cyano, and amino.

Useful compounds include those where $R^4$ and $R^6$ are both hydrogen and $R^5$ and $R^7$ are as defined above. Further useful compounds include those where $R^4$ and $R^6$ are both hydrogen and $R^5$ and $R^7$ are independently selected from the group consisting of hydrogen, methyl, ethyl, propyl, isopropyl, halogen, methoxy, ethoxy, trifluoromethyl, trifluoromethoxy, cyano, amino, and dimethylamino. Advantageously, $R^4$ and $R^6$ are both hydrogen and $R^5$ and $R^7$ are both fluorine. Preferably, either or both $R^5$ and $R^7$ are at the para-position of the respective phenyl rings.

Compounds useful in the present invention are represented by Formula V:

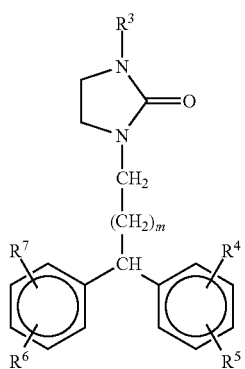

or a pharmaceutically acceptable salt, prodrug, or solvate thereof, wherein $R^3$-$R^7$ and m are as defined above for Formula I. In Formula V, preferred values for $R^3$-$R^7$ and m are those described above for Formula I.

In one embodiment, compounds useful in the present invention are compounds represented by Formula VI:

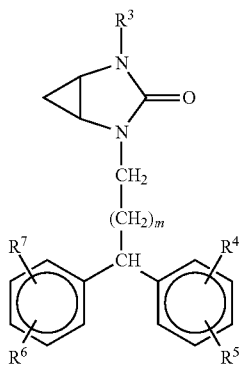

VI or a pharmaceutically acceptable salt, prodrug, or solvate thereof, wherein $R^3$-$R^7$ and m are as defined above for Formula I. Preferred values for $R^3$-$R^7$ and m are those described above for Formula I. Useful compounds of Formula VI include those where $R^3$ is (vi) or (vii), i.e.,

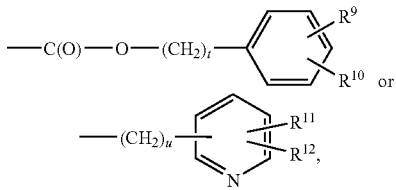

where t, u, and $R^9$-$R^{12}$ are as defined above.

In another embodiment, compounds useful in the present invention are represented by Formula VII:

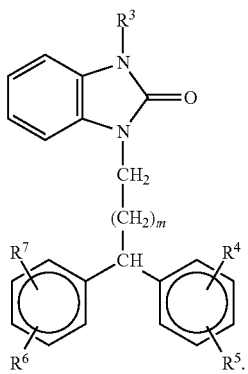

VII or a pharmaceutically acceptable salt, prodrug or solvate thereof, wherein $R^3$-$R^7$ and m are as defined above for Formula I. Preferred values for $R^3$-$R^7$ and m are those described above for Formula I. Useful compounds of Formula VII include those where $R^3$ is (iv), i.e., —$(CH_2)_p$—Y, where Y is

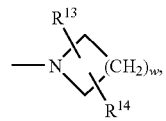

where $R^{13}$, $R^{14}$, and w are as defined above.

Further useful compounds of Formula VII include those where $R^3$ is (vii)

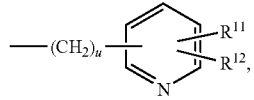

where u, $R^{11}$, and $R^{12}$ are as defined above.

In one embodiment, compounds useful in the present invention are compounds of any one of Formula II-IV, where Z is $Z^2$, —$CH_2$—$(CH_2)_n$—$R^8$, wherein $R^8$ and n are as defined above. $R^3$ is as defined above.

Useful compounds include those where $R^8$ is phenyl optionally substituted with one, two or three substituents independently selected from the group consisting of alkyl, alkoxy, halogen, hydroxy, haloalkyl, haloalkoxy, hydroxyalkyl, cyano, amino, aminoalkyl, alkylamino, and dialkylamino; preferably independently selected from the group consisting of alkyl, alkoxy, halogen, haloalkyl, haloalkoxy, amino, alkylamino, and dialkylamino; and more preferably independently selected from the group consisting of $C_{1-6}$ alkyl, $C_{1-6}$ alkoxy, halogen, halo($C_{1-3}$)alkyl, halo($C_{1-3}$) alkoxy, amino, $C_{1-3}$ alkylamino, and di($C_{1-3}$)alkylamino. Advantageously, $R^8$ is phenyl optionally substituted with one, two or three substituents independently selected from the group consisting of methyl, ethyl, propyl, iso-propyl, methoxy, ethoxy, halogen (especially fluorine), trifluoromethyl, trifluoromethoxy, and dimethylamino. Useful compounds include those where $R^8$ is phenyl substituted with one, two or three substituents as defined above.

Useful compounds include those where $R^8$ is pyridyl, especially pyrid-2-yl, pyrid-3-yl, or pyrid-4-yl, optionally substituted with one or two substituents independently selected from the group consisting of alkyl, halogen, haloalkyl, haloalkoxy, and alkoxy; preferably independently selected from the group consisting of alkyl, alkoxy, and haloalkoxy; and more preferably selected from the group consisting of $C_{1-6}$ alkyl, $C_{1-6}$ alkoxy, and halo($C_{1-3}$)alkoxy. Advantageously, $R^8$ is pyridyl optionally substituted with one or two substituents independently selected from the group consisting of methyl, ethyl, propyl, isopropyl, methoxy, ethoxy, trifluoromethoxy, and 2,2,2-trifluoroethoxy. Useful compounds include those where $R^8$ is pyridyl substituted with one or two substituents as defined above.

Useful compounds include those where $R^8$ is thiazolyl, especially thiazol-4-yl or thiazol-5-yl, optionally substituted with one or two substituents independently selected from the group consisting of alkyl, alkoxy, halogen, and haloalkyl; preferably independently selected from the group consisting of $C_{1-4}$ alkyl, $C_{1-4}$ alkoxy, halogen, and halo($C_{1-3}$)alkyl; and more preferably independently selected from the group consisting of methyl, ethyl, iso-propyl, methoxy, ethoxy, halogen (especially fluorine), and trifluoromethyl.

Preferably, n is 0 or 1.

Exemplary compounds that may be employed in the methods of the present invention include:

1-(3,3-diphenylpropyl)-3-phenylimidazolidin-2-one;
1-[4,4-bis(4-fluorophenyl)butyl]-3-phenylimidazolidin-2-one;
1-[4,4-bis(4-fluorophenyl)butyl]-3-(3-phenylprop-2-enyl) imidazolidin-2-one;
1-[4,4-bis(4-fluorophenyl)butyl]-3-(pyridin-3-ylmethyl) imidazolidin-2-one;
1-[4,4-bis(4-fluorophenyl)butyl]-3-(pyridin-4-ylmethyl) imidazolidin-2-one;
1-[4,4-bis(4-fluorophenyl)butyl]-3-(pyridin-2-ylmethyl) imidazolidin-2-one;
1-[4,4-bis(4-fluorophenyl)butyl]-3-methylimidazolidin-2-one;
1-[4,4-bis(4-fluorophenyl)butyl]-3-cyclopropylimidazolidin-2-one;
1-[4,4-bis(4-fluorophenyl)butyl]-3-[2-(pyrrolidin-1-yl) ethyl]imidazolidin-2-one;
1-[4,4-bis(4-fluorophenyl)butyl]-3-[2-(piperidin-1-yl)ethyl] imidazolidin-2-one;
1-[4,4-bis(4-fluorophenyl)butyl]-imidazolidin-2-one;
and pharmaceutically acceptable salts, prodrugs and solvates thereof.

Other exemplary compounds useful in the methods of the present invention include:

2-[4,4-bis(4-fluorophenyl)butyl]-4-methyl-2,4-diazabicyclo [3.1.0]hexan-3-one;
2-[4,4-bis(4-fluorophenyl)butyl]-4-(pyridin-2-yl)methyl-2, 4-diazabicyclo[3.1.0]hexan-3-one;
2-[4,4-bis(4-fluorophenyl)butyl]-4-benzyloxycarbonyl-2,4-diazabicyclo[3.1.0]hexan-3-one;
2-[4,4-bis(4-fluorophenyl)butyl]-2,4-diaza-bicyclo[3.1.0] hexan-3-one;
and pharmaceutically acceptable salts, prodrugs and solvates thereof.

Other exemplary compounds useful in the methods of the present invention include:

1-[4,4-bis(4-fluorophenyl)butyl]-3-[2-(piperidin-1-yl) ethyl]-1,3-dihydro-benzoimidazol-2-one;
1-[4,4-bis(4-fluorophenyl)butyl]-3-(pyridin-3-yl)methyl-1, 3-dihydro-benzoimidazol-2-one;
1-[4,4-bis(4-fluorophenyl)butyl]-3-(pyridin-4-yl)methyl-1, 3-dihydro-benzoimidazol-2-one;
1-[4,4-bis(4-fluorophenyl)butyl]-3-(pyridin-2-yl)methyl-1, 3-dihydro-benzoimidazol-2-one;
1-[4,4-bis(4-fluorophenyl)butyl]-3-(pyridin-4-yl)-1,3-dihydro-benzoimidazol-2-one;
1-[4,4-bis(4-fluorophenyl)butyl]-1,3-dihydro-benzoimidazol-2-one;
and pharmaceutically acceptable salts, prodrugs and solvates thereof.

Useful cycloalkyl groups are $C_{3-12}$ cycloalkyl. Typical cycloalkyl groups include cyclopropyl, cyclobutyl, cyclopentyl, cyclohexyl, cycloheptyl, and cyclooctyl.

Useful halo or halogen groups include fluorine, chlorine, bromine and iodine.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, iso-butyl, 3-pentyl, hexyl and octyl groups.

Useful haloalkyl groups include $C_{1-10}$ alkyl groups substituted by one or more fluorine, chlorine, bromine or iodine atoms (e.g., fluoromethyl, difluoromethyl, trifluoromethyl, pentafluoroethyl, 1,1-difluoroethyl and trichloromethyl groups).

Useful hydroxyalkyl groups include $C_{1-10}$ alkyl groups substituted by hydroxy (e.g., hydroxymethyl, hydroxyethyl, hydroxypropyl and hydroxybutyl groups).

Useful aminoalkyl groups include $C_{1-10}$ alkyl groups substituted by amino (e.g., aminomethyl, aminoethyl, aminopropyl and aminobutyl groups).

Useful alkoxy groups include oxygen substituted by one of the $C_{1-10}$ alkyl groups mentioned above.

Useful haloalkoxy groups include oxygen substituted by one of the $C_{1-10}$ haloalkyl groups mentioned above (e.g., fluoromethoxy, difluoromethoxy, trifluoromethoxy, and 2,2, 2-trifluoroethoxy).

The term "heterocyclic" is used herein to mean a saturated 3-7 membered monocyclic ring system having carbon atoms and from one to four heteroatoms independently selected from the group consisting of O, N, and S, wherein the nitrogen and sulfur heteroatoms can be optionally oxidized, the nitrogen can be optionally quaternized, and wherein the heterocyclic ring can be substituted on a carbon atom or on a nitrogen atom if the resulting compound is stable. Examples include, but are not limited to, aziridine, pyrrolidine, piperidine, piperazine, morpholine, imidazolidine, pyrazolidine, oxazolidine, and the like.

Useful alkylamino and dialkylamino groups are —NHR$^{15}$ and —NR$^{15}$R$^{16}$, wherein R$^{15}$ and R$^{16}$ are each independently selected from a $C_{1-10}$ alkyl group.

As used herein, the term "amino" or "amino group" refers to —NH$_2$.

The invention disclosed herein is also meant to encompass prodrugs of the disclosed compounds. Prodrugs are considered to be any covalently bonded carriers that release the active parent drug in vivo. Non-limiting examples of prodrugs include esters or amides of compounds of Formulae I-VII having hydroxyalkyl or aminoalkyl as a substituent, and these may be prepared by reacting such compounds with anhydrides such as succinic anhydride.

The invention disclosed herein is also meant to encompass the disclosed compounds being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Isotopically-labeled compounds of the present invention can be prepared by methods known in the art.

The present invention is also directed specifically to $^{3}$H and $^{14}$C radiolabeled compounds of Formula I-VII, and their use as radioligands for their binding site on the calcium channel. For example, one use of the labeled compounds of the invention is the characterization of specific receptor binding. Another use of the labeled compounds of the present invention is an alternative to animal testing for the evaluation of structure-activity relationships. The receptor assay is performed at a fixed concentration of a labeled compound of Formula I-VII and at increasing concentrations of a test compound in a competition assay. Tritiated compounds of Formula I-VII can be prepared by introducing tritium into the compound of Formula I-VII, for example, by catalytic dehalogenation with tritium. This method includes reacting a suitably halogen-substituted precursor of a compound of Formula I-VII with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}$C-labeled compounds can be prepared by employing starting materials having a $^{14}$C carbon.

Some of the compounds disclosed herein may contain one or more asymmetric centers and may thus give rise to enantiomers, diastereomers, and other stereoisomeric forms. The present invention is meant to encompass all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The invention disclosed herein also encompasses all salts of the disclosed compounds, including all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts can be formed by mixing a solution of the compound of the present invention with a solution of a pharmaceutically acceptable non-toxic base such as sodium hydroxide, potassium hydroxide, choline hydroxide, sodium carbonate and the like.

The invention disclosed herein is also meant to encompass solvates of the disclosed compounds. One type of solvate is a hydrate. Solvates do not contribute significantly to the physiological activity or toxicity of the compounds and as such can function as pharmacological equivalents.

Since compounds of Formula I-VII are blockers of calcium ($Ca^{2+}$) channels, a number of diseases and conditions mediated by calcium ion influx can be treated by employing these compounds. Therefore, the present invention provides a method of treating, preventing or ameliorating stroke, head trauma, epilepsy, pain (e.g., acute pain or chronic pain, which includes, but is not limited to, neuropathic pain and inflammatory pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia. In each instance, such methods of treatment, prevention, or amelioration require administering to an animal in need of such treatment, prevention or amelioration an effective amount of a calcium channel blocking compound of the present invention, or a pharmaceutically acceptable salt, prodrug or solvate thereof.

Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes. In each instance, the methods of the present invention require administering to an animal in need of such treatment an effective amount of a calcium channel blocking compound of the present invention, or a pharmaceutically acceptable salt, prodrug or solvate thereof.

Chronic somatic pain generally results from inflammatory responses to tissue injury such as nerve entrapment, surgical procedures, cancer or arthritis (Brower, *Nature Biotechnology* 2000; 18: 387-391). Although many types of inflammatory pain are currently treated with NSAIDs, there is much room for improved therapies.

The inflammatory process is a complex series of biochemical and cellular events activated in response to tissue injury or the presence of foreign substances (Levine, *Inflammatory Pain, In: Textbook of Pain*, Wall and Melzack eds., 3$^{rd}$ ed., 1994). Inflammation often occurs at the site of injured tissue, or foreign material, and contributes to the process of tissue repair and healing. The cardinal signs of inflammation include erythema (redness), heat, edema (swelling), pain and loss of function (ibid.). The majority of patients with inflammatory pain do not experience pain continually, but rather experience enhanced pain when the inflamed site is moved or touched. Inflammatory pain includes, but is not limited to, osteoarthritis and rheumatoid arthritis.

Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but is not limited to pain caused by nerve injury such as, for example, the pain from which diabetics suffer.

The present invention is also directed to a method for treating a disorder responsive to the blockade of calcium channels, and particularly the selective blockade of N-type calcium channels, in an animal suffering from said disorder, said method comprising administering to the animal an effective amount of a compound represented by any of defined Formulae I-VII.

The present invention is also directed to the use of a compound represented by any of defined Formulae I-VII for the manufacture of a medicament, in particular a medicament for treating a disorder responsive to the blockade of calcium channels, and particularly the selective blockade of N-type calcium channels, in an animal suffering from said disorder.

Furthermore, the present invention is directed to a method of modulating calcium channels, especially N-type calcium channels, in an animal in need thereof, said method comprising administering to the animal at least one compound represented by any of defined Formulae I-VII.

The present invention is also directed to the use of a compound represented by any of defined Formulae I-VII for the manufacture of a medicament, in particular a medicament for modulating calcium channels, especially N-type calcium channels, in an animal in need thereof.

Synthesis of Compounds

The compounds of the present invention may be prepared using methods known to those skilled in the art in view of this disclosure. For example, compounds of Formula I where Z is $Z^1$ and $R^1$ and $R^2$ are both hydrogen can be prepared as shown in Schemes 1-3.

Scheme 1

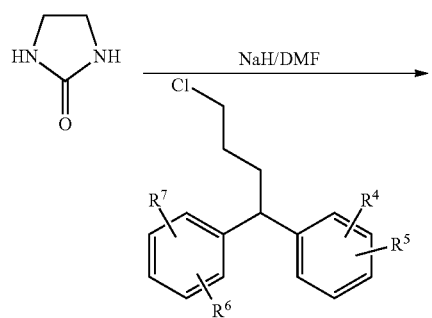

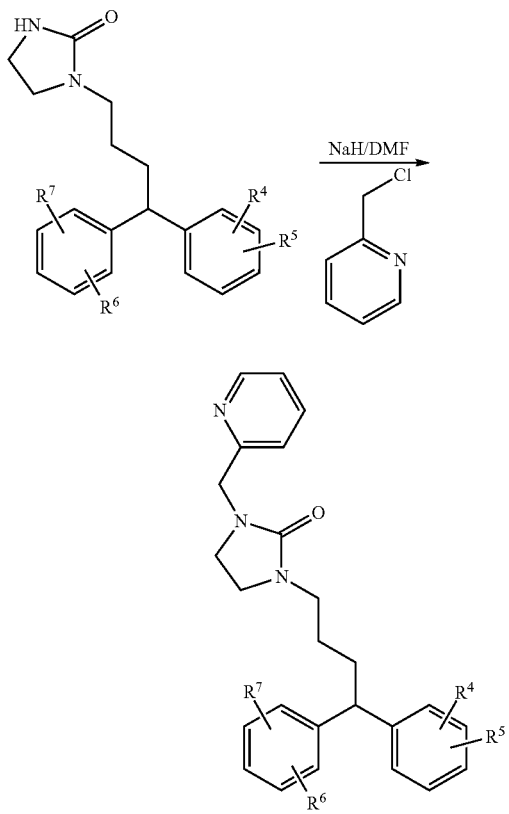

Imidazolidin-2-one derivatives of Formula I where Z is $Z^1$ and $R^1$ and $R^2$ are both hydrogen can be prepared as illustrated by exemplary reactions in Scheme 2 using the methods of 1) Chern, Jyh-Haur et al. (*Bioorganic & Medicinal Chemistry Letters* 14(20):5051-5056 (2004)) and 2) Shia, Kak-Shan et al. (*Journal of Medicinal Chemistry* 45(8):1644-1655 (2002)) as shown in Scheme 2.

Scheme 2

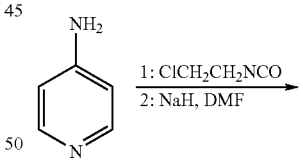

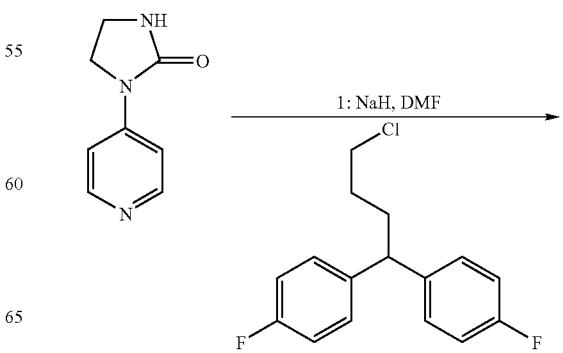

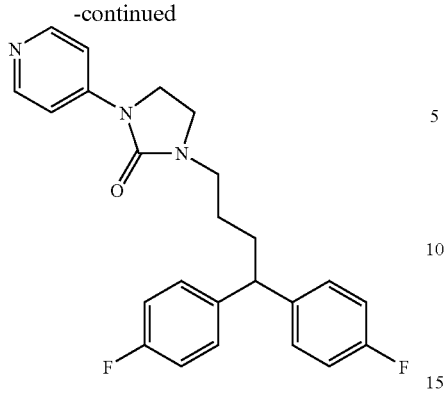

Imidazolidin-2-one derivatives of Formula I where Z is $Z^1$ and $R^1$ and $R^2$ are both hydrogen can also be prepared as illustrated by exemplary reactions in Scheme 3 using the methods of 1) Solomon, V. Raja et al. (*Bioorganic & Medicinal Chemistry* 13(6):2157-2165 (2005)), 2) Donati, Donato et al. (*Synthesis* 16:2518-2524 (2003)), and 3) Llopart, Carme Cantos et al. (*Canadian Journal of Chemistry* 82(11):1649-1661 (2004)) as shown in Scheme 3.

Compounds of Formula I where Z is $Z^1$ and $R^1$ and $R^2$ together with the carbon atoms to which they are attached form a fused cyclopropyl ring can be prepared as shown in Scheme 4:

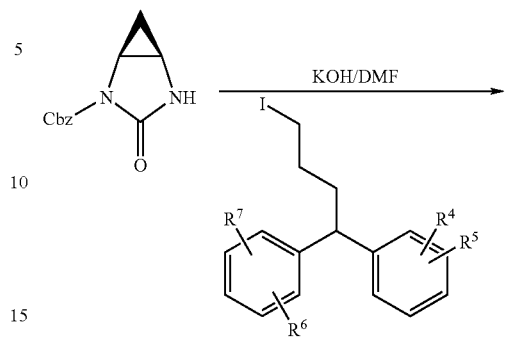

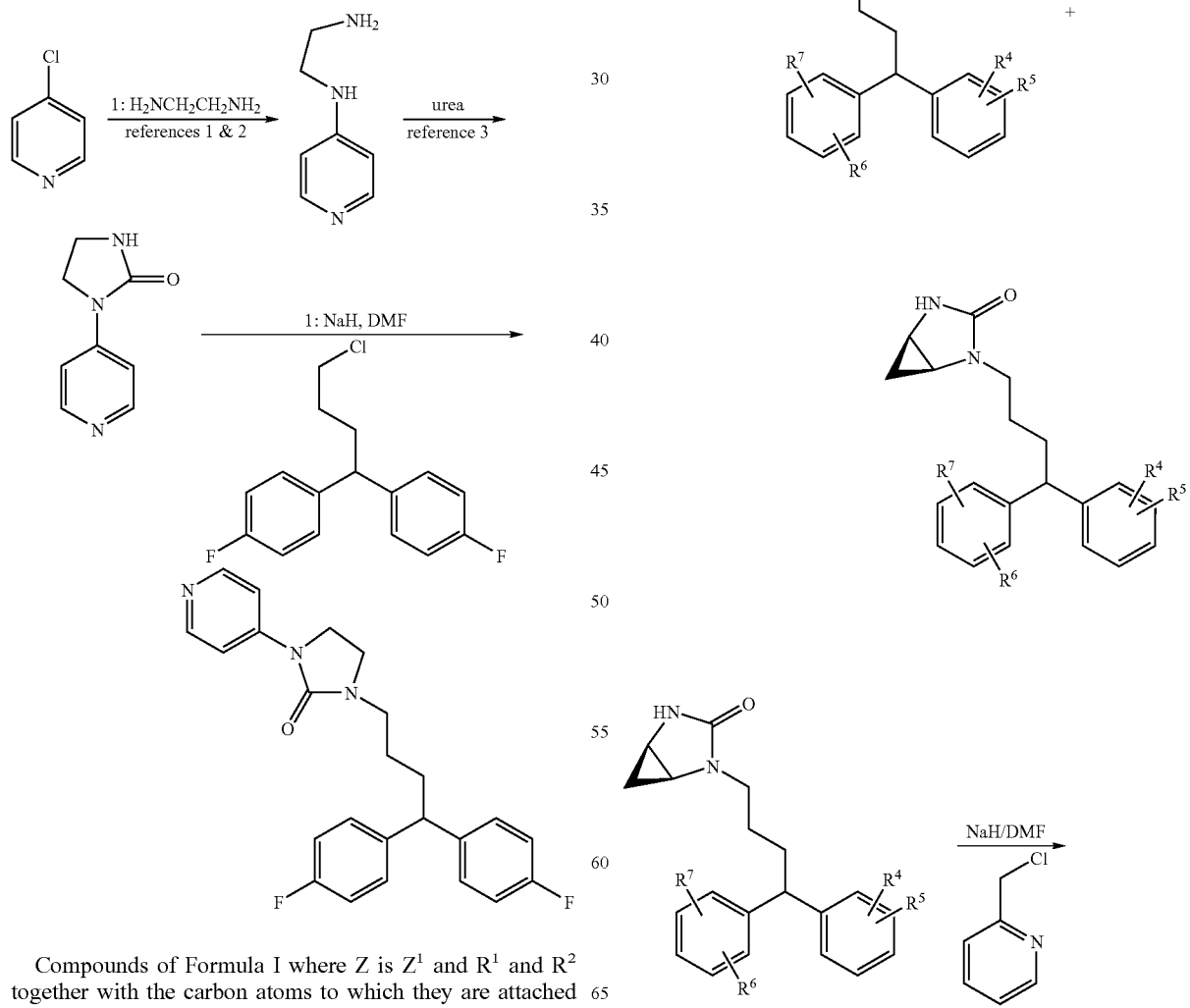

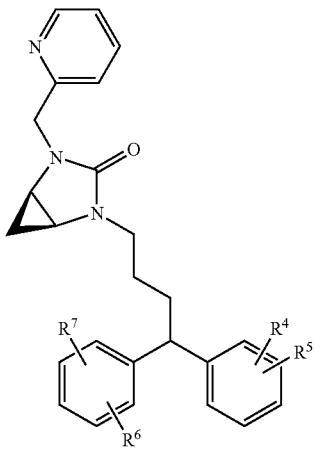

Compounds of Formula I where Z is $Z^1$ and $R^1$ and $R^2$ together with the carbon atoms to which they are attached form a fused phenyl ring can be prepared as shown in Scheme 5:

Scheme 5

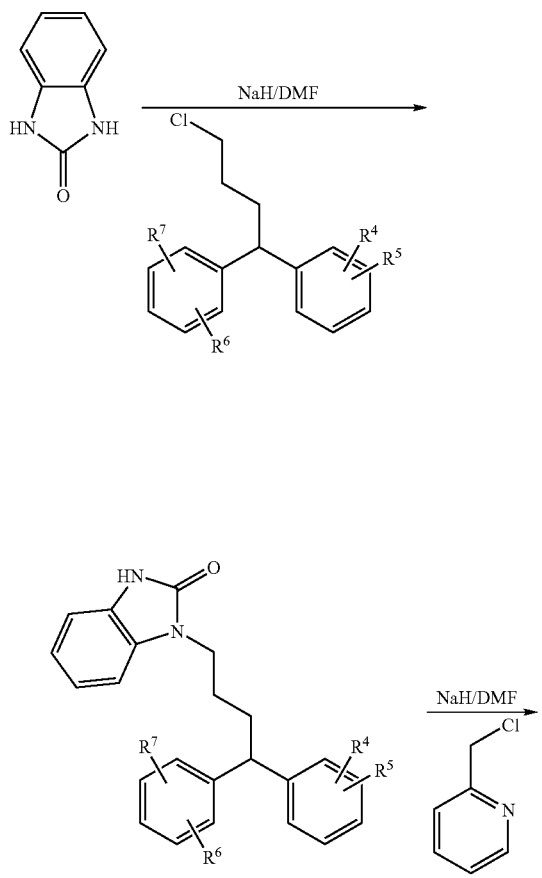

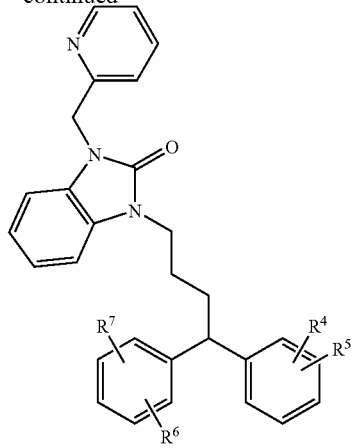

Compounds of Formula I where Z is $Z^2$ can be synthesized using methods similar to those described in Schemes 1-5 above.

Testing of Compounds

Compounds of the present invention were assessed by calcium mobilization and/or electrophysiological assays for calcium channel blocker activity. One aspect of the present invention is the discovery that the compounds herein described are selective N-type calcium channel blockers. Based upon this discovery, these compounds are considered useful in treating, preventing, or ameliorating migraine, epilepsy, a mood disorder, schizophrenia, a neurodegenerative disorder (such as, e.g., Alzheimer's disease, ALS, or Parkinson's disease), a psychosis, depression, anxiety, hypertension, or cardiac arrhythmia. The compounds of the present invention are also considered to be effective in treating, preventing or ameliorating pain, such as acute pain, chronic pain, which includes, but is not limited to, neuropathic pain and inflammatory pain, or surgical pain.

More specifically, the present invention is directed to compounds of Formulae I-VII that are blockers of calcium channels. According to the present invention, those compounds having preferred N-type calcium channel blocking properties exhibit an $IC_{50}$ of about 100 μM or less in the calcium mobilization and/or electrophysiological assays described herein. Preferably, the compounds of the present invention exhibit an $IC_{50}$ of 10 μM or less. More preferably, the compounds of the present invention exhibit an $IC_{50}$ of about 6 μM or less. Even more preferably, the compounds of the present invention exhibit an $IC_{50}$ of about 4 μM or less. Even more preferably, the compounds of the present invention exhibit an $IC_{50}$ of about 2 μM or less. Even more preferably, the compounds of the present invention exhibit an $IC_{50}$ of about 1.5 μM or less. Still more preferably, the compounds of the present invention exhibit an $IC_{50}$ of about 1.0 μM or less. Most preferably, the compounds of the present invention exhibit an $IC_{50}$ of about 0.7 μM or less.

Compounds of the present invention can be tested for their N-type and L-type $Ca^{2+}$ channel blocking activity by the following calcium mobilization and/or electrophysiological assays.

In one embodiment, compounds useful in the present invention are those represented by any one of Formulae I-VII that exhibit selectivity for N-type calcium channels over L-type calcium channels in the calcium mobilization and/or electrophysiological assays described herein. The phrase "selectivity for N-type calcium channels over L-type calcium channels" is used herein to mean that the ratio of an $IC_{50}$ for L-type channel blocking activity for a compound of the present invention over an $IC_{50}$ for N-type channel blocking activity for the same compound is more than 1, i.e., LTCC $IC_{50}$/NTCC $IC_{50}$>1. Preferably, compounds of the present invention exhibit an LTCC $IC_{50}$/NTCC $IC_{50}$ ratio of about 2 or more. More preferably, compounds of the present invention exhibit an LTCC $IC_{50}$/NTCC $IC_{50}$ ratio of about 4 or more. More preferably, compounds of the present invention exhibit an LTCC $IC_{50}$/NTCC $IC_{50}$ ratio of about 6 or more. More preferably, compounds of the present invention exhibit an LTCC $IC_{50}$/NTCC $IC_{50}$ ratio of about 9 or more. More preferably, compounds of the present invention exhibit an LTCC $IC_{50}$/NTCC $IC_{50}$ ratio of about 15 or more. More preferably, compounds of the present invention exhibit an LTCC $IC_{50}$/NTCC $IC_{50}$ ratio of about 30 or more. More preferably, compounds of the present invention exhibit an LTCC $IC_{50}$/NTCC $IC_{50}$ ratio of about 60 or more. Advantageously, compounds of the present invention exhibit an LTCC $IC_{50}$/NTCC $IC_{50}$ ratio of about 100 or more.

Calcium Mobilization and Electrophysiological Assay Protocols:

Cell maintenance and differentiation. Unless noted otherwise, cell culture reagents were purchased from Life Technologies of Rockville, Md. IMR32 cells (American Type Culture Collection, ATCC, Manassas, Va.) were routinely cultured in growth medium consisting of minimum essential medium containing 10% fetal bovine serum (FBS, Hyclone, Logan, Utah), 100 U/mL penicillin, 100 µg/mL streptomycin, 2 mM L-glutamine, 1 mM sodium pyruvate, and 1×MEM non-essential amino acids. 80-90% confluent flasks of cells were differentiated using the following differentiation medium: Growth medium plus 1 mM dibutyryl cyclic AMP (Sigma, St. Louis, Mo.), and 2.5 µM bromodeoxyuridine (Sigma). Cells were differentiated for 8 days by replacing differentiation medium every 2-3 days.

A7r5 (ATCC) cells were maintained and routinely cultured in A7r5 growth medium consisting of Dulbecco's Modified Eagles Medium containing 10% FBS, 100 U/mL penicillin, 100 µg/mL streptomycin, 4 mM L-glutamine, and 0.15% sodium bicarbonate. 80-90% confluent flasks of cells were differentiated using the following differentiation medium: A7r5 Growth Medium plus 1 mM dibutyryl cyclic AMP (Sigma). Cells were differentiated for 8 days by replacing differentiation medium every 2-3 days.

FLIPR Calcium Mobilization Assay for N-type Calcium Channel. One day prior to performing this assay, differentiated IMR32 cells were treated with 1×CellStripper, and seeded on poly-D-lysine-coated 96-well clear-bottom black plates (Becton Dickinson, Franklin Lakes, N.J.) at 200,000 cells/well. On the day of the assay, the cell plates were washed with IMR32 buffer (127 mM NaCl, 1 mM KCl, 2 mM $MgCl_2$, 700 µM $NaH_2PO_4$, 5 mM $CaCl_2$, 5 mM $NaHCO_3$, 8 mM HEPES, 10 mM glucose, pH 7.4), then pre-stimulated with KCl and loaded as follows: 0.05 mL of IMR32 buffer, 0.05 mL of each compound tested diluted in IMR32 buffer containing 20 µM nitrendipine (Sigma), and 0.1 mL KCl dissolved in IMR32 buffer, plus Fluo-4 were added (3 µM final concentration, Molecular Probes, Eugene, Oreg.). Final test compound concentrations ranged from about 846 µM to about 17 µM, final nitrendipine concentration was 5 µM, and final KCl concentration was 90 mM. After 1 hour, the cells were washed twice with 0.05 mL of each compound tested in nitrendipine-containing IMR32 buffer (no KCl or Fluo-4), and then replaced with 0.1 mL of each compound tested in nitrendipine-containing IMR32 buffer. Plates were then transferred to a Fluorimetric Imaging Plate Reader (FLIPR[96], Molecular Devices, Inc., Sunnyvale, Calif.) for assay. The FLIPR measured basal Fluo-4 fluorescence for 315 seconds (i.e., 5 minutes and 15 seconds), then added 0.1 mL KCl agonist dissolved in IMR32 buffer and measured fluorescence for another 45 seconds. Final test compound concentrations on the cells after FLIPR read ranged from about 846 µM to about 17 µM, final nitrendipine concentration was 5 µM, and final KCl concentration was 90 mM. Data were collected over the entire time course and analyzed using Excel, Graph Pad Prism (version 3.02, Graph Pad, San Diego, Calif.), or Activity Base (version 5.1, IDBS, Parsippany, N.J.) software.

FLIPR Calcium Mobilization Assay for L-type Calcium Channel. One day prior to performing this assay, differentiated A7r5 cells were trypsinized, then seeded on tissue culture treated 96-well clear-bottom black plates (Becton Dickinson, Franklin Lakes, N.J.) at a dilution of 1:1 from a confluent T150 $cm^2$ flask. On the day of the assay, the plates were washed with A7r5 wash buffer (127 mM NaCl, 2 mM $MgCl_2$, 700 µM $NaH_2PO_4$, 5 mM $CaCl_2$, 5 mM $NaHCO_3$, 8 mM HEPES, 10 mM glucose, pH 7.4), then loaded with 0.1 mL of A7r5 wash buffer containing Fluo-4 (3 µM final concentration, Molecular Probes, Eugene, Oreg.). After 1 hour, the cells were washed with 0.1 mL A7r5 wash buffer and resuspended in 0.05 mL A7r5 assay buffer that was composed of A7r5 wash buffer plus 50 µM valinomycin (Sigma). Plates were then transferred to a FLIPR[96] for assay. The FLIPR measured basal Fluo-4 fluorescence for 15 seconds, then added 0.05 mL of each compound tested diluted in A7r5 assay buffer at final concentrations ranging from about 846 µM to about 17 µM. Fluo-4 fluorescence was then measured for 5 minutes. 0.1 mL KCl agonist dissolved in A7r5 assay buffer was then added to the cells to produce a final concentration of 90 mM KCl, and fluorescence was measured for another 45 seconds. Data were collected over the entire time course and analyzed using Excel, Graph Pad Prism, or Activity Base software.

Cloning of N- and L-type calcium channel subunit open reading frame cDNAs. Five cDNAs encoding subunits of the rat N- or L-type calcium channels were cloned by PCR amplification in order to reconstitute functional channels in a heterologous system. These were the alpha1b (α1b), beta1 (β1), beta3 (β3), alpha2delta (α2δ), and alpha1c (α1c) subunit cDNAs. The alpha1b subunit cDNA has been described by Dubel et al. in *Proc. Natl. Acad. Sci. U.S.A* 89: 5058-5062 (1992). The beta1 subunit cDNA has been described by Pragnell et al. in *FEBS Lett.* 291: 253-258 (1991). The beta3 subunit cDNA has been described by Castellano et al. in *J. Biol. Chem.* 268: 12359-12366 (1993). The alpha2delta subunit cDNA has been described by Kim et al. in *Proc. Natl. Acad. Sci. U.S.A.* 89: 3251-3255 (1992). The alpha1c subunit cDNA has been described by Koch et al. in *J. Biol. Chem.* 265: 17786-17791 (1990).

The 7.0 kb cDNA containing the entire α1b open reading frame (ORF) was PCR amplified as two overlapping cDNA fragments, i.e., a 2.7 kb 5' fragment and a 4.4 kb 3' fragment. The 5' fragment was amplified from rat brain cDNA using primers 1 (SEQ ID NO:1, TABLE 1) and 2 (SEQ ID NO:2, TABLE 1), and the 3' fragment was amplified from rat spinal cord cDNA using primers 3 (SEQ ID NO:3, TABLE 1) and 4 (SEQ ID NO:4, TABLE 1). The two fragments were joined by ligation at a common restriction site to create the entire 7.0 kb cDNA. This ORF encodes the protein isoform generated by alternative splicing termed "+A ΔSFMG ΔET" according to the nomenclature of Lin et al. (*Neuron* 18: 153-166 (1997)). The entire cDNA was sequenced with redundant coverage on both strands. The cDNA was then inserted into the mammalian expression vector pcDNA6.2DEST (Invitrogen, Carlsbad Calif.) by homologous recombination using the Gateway system (Invitrogen).

The 1.8 kb cDNA encoding the β1 subunit, the 1.45 cDNA encoding the beta3 subunit, and the 3.3 kb cDNA encoding the alpha2delta subunit were cloned by PCR amplification from rat spinal cord cDNA (β1) or brain cDNA (β3, α2δ).

Primers 5 (SEQ ID NO:5, TABLE 1) and 6 (SEQ ID NO:6, TABLE 1) were used for the β1 cDNA amplification; primers 7 (SEQ ID NO:7, TABLE 1) and 8 (SEQ ID NO:8, TABLE 1) were used for the β3 cDNA amplification; and primers 9 (SEQ ID NO:9, TABLE 1) and 10 (SEQ ID NO:10, TABLE 1) were used for the α2δ cDNA amplification. PCR products were subcloned and fully sequenced on both strands. Clones matching the reference sequence (β1: NM_017346; β3: NM_012828; α2δ: M86621) and the gene's GenBank rat genomic DNA sequences were recombined into the mammalian expression vector pcDNA3.2DEST (β1, β3) or pcDNA3.1-Zeo (α2δ), which had been modified to a vector compatible with the Gateway recombination system using the Gateway vector adaptor kit (Invitrogen). Proper recombination was confirmed by sequencing of recombinogenic regions. For β3 expression vector, proper protein expression was confirmed by Western blot analysis of lysates of transfected HEK293 cells using a rabbit polyclonal antiserum directed against the rat β3 subunit (USA Biological).

The 6.5 kb cDNA encoding the L-type calcium channel α1c subunit was cloned by PCR amplification from rat heart cDNA using primers 11 (SEQ ID NO:11, TABLE 1) and 12 (SEQ ID NO:12, TABLE 1). The PCR fragment was subcloned and fully sequenced on both strands to confirm its identity. A clone matching consensus reference sequence M59786 and rat genomic DNA sequences was recombined into the mammalian expression vector pcDNA6.2DEST. Sequences around the recombinogenic region were sequenced to confirm accurate recombination into the expression vector.

TABLE 1

| PRIMER SEQUENCE | SEQ ID NO. |
| --- | --- |
| CACC ATG GTC CGC TTC GGG GAC | 1 |
| CCG TTC AGT GGC CTC CTC C | 2 |
| C TAG CAC CAG TGA TCC TGG TCTG | 3 |
| AGT GCG TTG TGA GCG CAG TA | 4 |
| CAC CAT GGT CCA GAA GAG CGG | 5 |
| TCTCAGCGGATGTAGACGCCT | 6 |
| CAC CAT GTA TGA CGA CTC CTA C | 7 |
| GGT GGT CAG TAG CTG TCC TTA GG | 8 |
| CAC CAT GGC TGC TGG CTG CCT | 9 |
| AGA GGG TCA CCA TAG ATA GTG TCT G | 10 |
| CACCATGATTCGGGCCTTCGCT | 11 |
| AGCCTGCGGACTACAGGTTGCTGAC | 12 |

N-type Recombinant Cell Line Development. N-type calcium channel expressing HEK-293 cells were created in two stages. Stage 1 was created as follows. The rat α1b, and β3 cDNA expression constructs (2.5 μg each) were co-transfected into human embryonic kidney (HEK-293) cells by Lipofectamine Plus reagent (Invitrogen), as per manufacturer's instructions. 24 hours later, cells were split in limiting dilution into multiple 96-well plates in selection media containing 20 μg/mL blasticidin and 500 μg/mL geneticin, and incubated for 3 weeks at 37° C., 5% $CO_2$, 95% humidity. Plates containing ≦1 clone per well were cultured until wells positive for single clones were confluent. Individual clones were then arrayed into columns of a destination 96-well plate, and partly split into 6-well plates for culture maintenance. Array plates were washed once with IMR32 buffer and cells loaded for 1 hour with 0.1 mL of IMR32 buffer containing Fluo-4 (3 μM final concentration, Molecular Probes). Then they were washed twice with 0.1 mL of IMR32 buffer, and replaced with 0.1 mL IMR32 buffer. Plates were then transferred to a FLIPR[96] for assay. The FLIPR measured basal Fluo-4 fluorescence for 315 seconds, then added 0.1 mL KCl agonist dissolved in IMR32 buffer and measured fluorescence for another 45 seconds. Final KCl concentration was 90 mM. Data were collected over the entire time course and analyzed using Excel, Graph Pad Prism, or Activity Base software. The clone with the greatest signal-to-noise ratio, best stability of response with passage number, and best adhesion to PDL precoated plates (Becton Dickinson) was expanded, characterized and used for stage 2 cell line development.

Stage 2 of N-type cell line development was carried out as follows. The rat α2δ cDNA expression construct (5 μg each) was transfected into the stage 1 N-type clonal cell line by Lipofectamine Plus reagent (Invitrogen), as per manufacturer's instructions. 24 hours later, cells were split in limiting dilution into multiple 96-well plates in selection media containing 20 μg/mL blasticidin, 500 μg/mL geneticin, and 250 μg/mL zeocin and incubated for 3 weeks at 37° C., 5% $CO_2$, 95% humidity. Plates containing ≦1 clone per well were cultured and handled according to the same steps and procedures described above for the stage 1 cell line. The three clones with the greatest signal-to-noise, best stability of response with passage number, and best adhesion to PDL precoated plates (Becton Dickinson) were expanded, characterized and tested in electrophysiology for the best current size, N-type pharmacology, N-type characteristic current-voltage relationship and kinetics as described below.

N-type Electrophysiology in Recombinant Cells. For electrophysiological recording, the cells expressing α1b, β3 and α2δ subunits were seeded on 35-mm culture Petri dishes at a density of approximately $10^4$ cells/dish and kept in an incubator for up to three days for subsequent recordings. For recordings, the dishes were positioned on the stage of an inverted microscope (Nikon, Eclipse E600, Japan) and superfused with a bath solution comprised of $BaCl_2$ (11 mM), $MgCl_2$ (1.5 mM), HEPES (10 mM), TEA chloride (120 mM), glucose (10 mM) adjusted to pH 7.4 with KOH. Whole-cell voltage-clamp recordings were made using conventional patch-clamp techniques (Hamill et al., *Pfluegers Arch.* 391: 85-100 (1981)) at room temperature (22-24° C.). The patch-clamp pipettes were pulled from WPI, thick-walled borosilicate glass (WPI, Sarasota, Fla.). Currents were recorded using an Axopatch 200A amplifier (Axon Instruments, Union City, Calif.) and were leak-subtracted (P/4), low-pass filtered (1 kHz, 4-pole Bessel), digitized (20-50-μs intervals), and stored using Digidata 1200 B interface and Pclamp8.0/Clampex software (Axon Instruments, Union City, Calif.). The pipettes were back-filled with internal solution containing CsCl (110 mM), $MgCl_2$ (3 mM), EGTA (3 mM), HEPES (40 mM), Mg-ATP (4 mM), $Na_2GTP$ (0.5 mM), and adjusted to pH 7.2 with CsOH. The pipette resistance ranged from 2 to 3 MOhm and was compensated by 75-80% by the built-in electronic circuitry.

Currents were elicited by stepping from a holding potential of −90 mV to 0 mV for 20 ms every 20 sec. At the −90 mV membrane voltage about 50% of channels were in the inactivated state, and thus contact with a blocker would involve interaction with both resting and inactivated channels. Every drug was applied at 3 to 4 concentrations increasing in a cumulative manner. Fractional inhibition levels in steady-state were used to draw the partial inhibition concentration curves to get the $IC_{50}$ (i.e. concentration causing 50% reduction in the size of the response) values at −90 mV.

Stock solutions of each test compound were prepared using DMSO. Serial dilutions to desired concentrations were done with bath solution; concentration of DMSO in final solutions was 0.1%. Drugs were applied by gravity flow using a plane multi-barrel array shooter positioned 0.5 mm apart from the cell.

All curve fittings were carried out using Origin software (version 5.0, Microcal). A Hill equation was fit to the concentration-inhibition curves to determine $IC_{50}$ values.

N-type Electrophysiology in Neuronal Cells. To determine dissociation constants in resting versus inactivated state for N-type calcium channels, neuronal cells that endogenously express N-type calcium channels can be used. For electrophysiological recording, the neuronal cells expressing N-type calcium channels are seeded on 35-mm culture Petri dishes at a density of approximately $10^4$ cells/dish and kept in an incubator for up to three days for subsequent recordings. For recordings, the dishes are positioned on the stage of an inverted microscope (Nikon, Eclipse E600, Japan) and superfused with a bath solution comprised of $BaCl_2$ (11 mM), $MgCl_2$ (1.5 mM), HEPES (10 mM), TEA chloride (120 mM), glucose (10 mM) adjusted to pH 7.4 with KOH. Whole-cell voltage-clamp recordings are made using conventional patch-clamp techniques (Hamill et al., *Pfluegers Arch.* 391: 85-100 (1981)) at room temperature (22-24° C.). The patch-clamp pipettes are pulled from WPI, thick-walled borosilicate glass (WPI, Sarasota, Fla.). Currents are recorded using an Axopatch 200A amplifier (Axon Instruments, Union City, Calif.) and leak-subtracted (P/4), low-pass filtered (1 kHz, 4-pole Bessel), digitized (20-50 μs intervals), and stored using Digi-data 1200 B interface and Pclamp8.0/Clampex software (Axon Instruments, Union City, Calif.). The pipettes are back-filled with internal solution containing CsCl (110 mM), $MgCl_2$ (3 mM), EGTA (3 mM), HEPES (40 mM), Mg-ATP (4 mM), $Na_2GTP$ (0.5 mM), and adjusted to pH 7.2 with CsOH. The pipette resistance ranges from 2 to 3 MOhm and is compensated by 75-80% by the built-in electronic circuitry.

Currents are elicited by stepping from a holding potential of −90 mV to 0 mV for 20 ms every 10 sec. At the −90 mV membrane voltage a proportion of channels is in the inactivated state, and thus contact with a blocker would involve interaction with both resting and inactivated channels. This protocol is used as a first tier screen. For dissection of two components of inhibition (resting block with the apparent dissociation constant $K_r$ and inactivated state block with $K_i$), steady-state inactivation curves are collected using a double-pulse protocol. Three-second long depolarizing pre-pulse incrementing in 10 mV steps is followed by a 10 ms test pulse to 0 mV.

Stock solutions of each test compound are prepared using DMSO. Serial dilutions to desired concentrations are done with bath solution; concentration of DMSO in final solutions is 0.1%. Drugs are applied by gravity flow using a plane multi-barrel array shooter positioned ~1 mm apart from the cell.

All curve fittings can be carried out using Origin software (version 5.0, Microcal). A Hill equation is used to fit the concentration-response curves and to determine $IC_{50}$ values. A Boltzman equation is used to fit inactivation curves, returning half-inactivation voltage, $V_{0.5}$, slope p and the amplitude of current at the most negative voltage where eventually all channels are in the resting state. These parameters are used to calculate the apparent dissociation constants: $K_r=((Ab/Ac)/(1-(Ab/Ac))[b])$ where [b] is the drug concentration, Ac is the maximum test current amplitude in control conditions and Ab is the maximum test current amplitude in the presence of a blocker; $K_i=[b]/((exp(-(dx/p))*(1+([b]/K_r))-1)$ where dx is the difference between half-inactivation voltage V0.5 in the presence and absence of drug and p is the slope.

In Vivo Pharmacology

The compounds of the present invention can be tested for in vivo anticonvulsant activity after i.v., p.o., or i.p. injection using any of a number of anticonvulsant tests in mice, including the maximum electroshock seizure test (MES). Maximum electroshock seizures are induced in male NSA mice weighing between 15-20 g and in male Sprague-Dawley rats weighing between 200-225 g by application of current (for mice: 50 mA, 60 pulses/sec, 0.8 msec pulse width, 1 sec duration, D.C.; for rats: 99 mA, 125 pulses/sec, 0.8 msec pulse width, 2 sec duration, D.C.) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results can be treated in a quantal manner.

The compounds can be tested for their antinociceptive activity in the formalin model as described in Hunskaar, S., O. B. Fasmer, and K. Hole, *J. Neurosci. Methods* 14: 69-76 (1985). Male Swiss Webster NIH mice (20-30 g; Harlan, San Diego, Calif.) can be used in all experiments. Food is withdrawn on the day of experiment. Mice are placed in Plexiglass jars for at least 1 hour to acclimate to the environment. Following the acclimation period mice are weighed and given either the compound of interest administered i.p. or p.o., or the appropriate volume of vehicle (10% Tween-80) as control. Fifteen minutes after the i.p. dosing, and 30 minutes after the p.o. dosing mice are injected with formalin (20 μL of 5% formaldehyde solution in saline) into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as licking/biting between 0-5 minutes, and the late phase is measured from 15-50 minutes. Differences between vehicle and drug treated groups can be analyzed by one-way analysis of variance (ANOVA). A P value <0.05 is considered significant. Compounds are considered to be efficacious for treating acute and chronic pain if they have activity in blocking both the early and second phase of formalin-induced paw-licking activity.

Compounds can be tested for their potential to treat chronic pain (i.e., antiallodynic and antihyperalgesic activities) using the Chung model of peripheral neuropathy (Kim and Chung, Pain 50: 355-363 (1992)). Male Sprague-Dawley rats weighing between 200-225 g are anesthetized with halothane (1-3% in a mixture of 70% air and 30% oxygen), and their body temperature controlled during anesthesia through use of a homeothermic blanket. A 2-cm dorsal midline incision is then made at the L5 and L6 level, and the para-vertebral muscle groups retracted bilaterally. L5 and L6 spinal nerves are then exposed, isolated, and tightly ligated with 6-0 or 7-0 silk suture. A sham operation is performed exposing the contralateral L5 and L6 spinal nerves, without ligating, as a negative control.

Tactile Allodynia: Sensitivity to non-noxious mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hindpaw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 gms filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration.

Mechanical Hyperalgesia: Sensitivity to noxious mechanical stimuli can be measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein (*Biochemistry & Behavior* 31: 451-455 (1988)). The rat's paw is placed on a small platform, and weight is applied in a graded manner up to a maximum of 250 grams. The endpoint is taken as the weight at which the paw is completely withdrawn. PWT is determined once for each rat at each time point. PWT can be measured only in the injured paw, or in both the injured and non-injured paw. In one non-limiting embodiment, mechanical hyperalgesia associated with nerve injury induced pain (neuropathic pain) can be assessed in rats. Rats are tested prior to surgery to determine a baseline, or normal, PWT. Rats are tested again 2 to 3 weeks post-surgery, prior to, and at different times after (e.g. 1, 3, 5 and 24 hr) drug administration. An increase in PWT following drug administration indicates that the test compound reduces mechanical hyperalgesia.

Pharmaceutical Compositions

Although a compound of the present invention may be administered to a mammal in the form of a raw chemical without any other components present, the compound is preferably administered as part of a pharmaceutical composition containing the compound combined with a suitable pharmaceutically acceptable carrier. Such a carrier can be selected from pharmaceutically acceptable excipients and auxiliaries.

Compositions within the scope of the present invention include all compositions where a compound of the present invention is combined with a pharmaceutically acceptable carrier. In a preferred embodiment, the compound is present in the composition in an amount that is effective to achieve its intended therapeutic purpose. While individual needs may vary, a determination of optimal ranges of effective amounts of each compound is within the skill of the art. Typically, the compounds may be administered to mammal, e.g. human, orally at a dose of from about 0.0025 to about 1500 mg per kg body weight of the mammal, or an equivalent amount of a pharmaceutically acceptable salt thereof, per day to treat the particular disorder. A useful oral dose of a compound of the present invention administered to a mammal is from about 0.0025 to about 50 mg per kg body weight of the mammal, or an equivalent amount of the pharmaceutically acceptable salt thereof. For intramuscular injection, the dose is typically about one-half of the oral dose.

A unit oral dose may comprise from about 0.01 to about 50 mg, and preferably about 0.1 to about 10 mg, of the compound. The unit dose can be administered one or more times daily as one or more tablets, each containing from about 0.01 to about 50 mg of the compound, or an equivalent amount of a pharmaceutically acceptable salt or solvate thereof.

In one embodiment, a pharmaceutical composition of the present invention can be administered orally and is formulated into tablets, dragees, capsules or an oral liquid preparation.

Alternatively, a pharmaceutical composition of the present invention can be administered rectally, and is formulated in suppositories.

Alternatively, a pharmaceutical composition of the present invention can be administered by injection.

Alternatively, a pharmaceutical composition of the present invention can be administered transdermally.

Alternatively, a pharmaceutical composition of the present invention can be administered by inhalation or by intranasal administration.

Alternatively, a pharmaceutical composition of the present invention can be administered by the intravaginal route.

A pharmaceutical composition of the present invention can contain from about 0.01 to 99 percent by weight, and preferably from about 0.25 to 75 percent by weight, of active compound(s).

The present methods of the invention, such as the method for treating, preventing, or ameliorating a disorder responsive to the blockade of calcium channels in an animal in need thereof, can further comprise administering another therapeutic agent to the animal being administered a cyclourea compound of Formula I. In one embodiment, the other therapeutic agent is administered in an effective amount.

Effective amounts of the other therapeutic agents are known to those skilled in the art. However, it is well within the skilled artisan's purview to determine the other therapeutic agent's optimal effective-amount range. In one embodiment of the invention, where another therapeutic agent is administered to an animal, the effective amount of the compound of the present invention is less than its effective amount would be where the other therapeutic agent is not administered. In this case, without being bound by theory, it is believed that compounds of the present invention and the other therapeutic agent act synergistically to treat, prevent, or ameliorate a disorder or condition.

The other therapeutic agent can be, but is not limited to, an opioid agonist, a non-opioid analgesic, a non-steroidal anti-inflammatory agent, an antimigraine agent, a Cox-II inhibitor, a β-adrenergic blocker, an anticonvulsant, an antidepressant, an anticancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, and mixtures thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed 1996) and Glen R. Hanson, *Analgesic, Antipyretic and Anti Inflammatory Drugs* in Remington: *The Science and Practice of Pharmacy* Vol II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839, which is hereby incorporated by reference in its entirety. Examples of useful Cox II inhibitors include, but are not limited to, rofecoxib and celecoxib.

Examples of useful antimigraine agents include, but are not limited to, alpiropride, bromocriptine, dihydroergotamine, dolasetron, ergocomine, ergocominine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, and cisplatin.

Therapeutic agents useful for treating or preventing an addictive disorder include, but are not limited to, methadone, desipramine, amantadine, fluoxetine, buprenorphine, an opiate agonist, 3-phenoxypyridine, or a serotonin antagonist.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy or seizure include, but are not limited to, carbamazepine, ethosuximide, gabapentin, lamotrigine, phenobarbital, phenyloin, primidone, valproic acid, trimethadione, benzodiazepines, gamma-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a pruritic condition include, but are not limited to, naltrexone; nalmefene; danazol; tricyclics such as amitriptyline, imipramine, and doxepin; antidepressants such as those given below; menthol; camphor; phenol; pramoxine; capsaicin; tar; steroids; and antihistamines.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating or preventing ALS include, but are not limited to, baclofen, neurotrophic factors, riluzole, tizanidine, benzodiazepines such as clonazepan and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating or preventing vomiting include, but are not limited to, 5-HT3 receptor antagonists such as odansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, clomipramine, desipranine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A cyclourea compound of the present invention and the other therapeutic agent can act additively or, in one embodiment, synergistically. In one embodiment, a compound of the present invention is administered concurrently with another therapeutic agent; for example, a composition comprising an effective amount of a compound of Formulae I-VII, and an effective amount of another therapeutic agent can be administered. Alternatively, a composition comprising an effective amount of a compound of Formulae I-VII and a different composition comprising an effective amount of another therapeutic agent can be concurrently administered. In another embodiment, an effective amount of a compound of the present invention is administered prior or subsequent to administration of an effective amount of another therapeutic agent. In this embodiment, the compound of the present invention is administered while the other therapeutic agent exerts its therapeutic effect, or the other therapeutic agent is administered while the compound of the present invention exerts its preventive or therapeutic effect for treating, ameliorating or preventing a disorder or condition.

A pharmaceutical composition of the present invention can be administered to any animal that may experience the beneficial effects of a compound of the present invention. Foremost among such animals are mammals, e.g., humans and companion animals, although the invention is not intended to be so limited.

A pharmaceutical composition of the present invention can be administered by any means that achieves its intended purpose. For example, administration can be by the parenteral, subcutaneous, intravenous, intramuscular, intraperitoneal, transdermal, intranasal, rectal, intravaginal or buccal route, or by inhalation. Alternatively, or concurrently, administration can be by the oral route. The dosage administered and route of administration will vary, depending upon the circumstances of the particular subject, and taking into account such factors as age, health, and weight of the recipient, condition or disorder to be treated, kind of concurrent treatment, if any, frequency of treatment, and the nature of the effect desired.

A pharmaceutical composition of the present invention is preferably manufactured in a manner which is itself known, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate can be used. Dye stuffs or pigments may be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which may be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers may be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound may be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

Example 1

1-[4,4-Bis(4-fluorophenyl)butyl]-imidazolidin-2-one (3)

To a suspension of sodium hydride (0.72 g, 18 mmol) in DMF (20.0 mL) was added a solution of imidazolidin-2-one (1) (2.5 g, 30.0 mmol, Aldrich) in DMF (10.0 mL) at room temperature. The resulting mixture was stirred at room temperature for 45 minutes and then a solution of 4,4-bis(4-fluorophenyl)butyl chloride (2) (5.6 g, 10 mmol) in DMF (10.0 mL) was added. Then the mixture was stirred at 60° C. for 4 hours. After this period, the mixture was cooled to room temperature and quenched with water (20 mL). The mixture was extracted with ethyl acetate (100 mL×3). The organic layer was dried with anhydrous $Na_2SO_4$ and concentrated to give a crude sample. The crude sample was purified by column chromatography using ethyl acetate/hexane gradient as an eluent to give the title compound 3. MS: m/z 331. $^1$H NMR ($CDCl_3$): δ 7.16 (m, 4H), 6.96 (t, J=8 Hz, 4H), 4.36 (br, 1H), 3.91 (t, J=8 Hz, 1H), 3.38 (m, 2H), 3.32 (m, 2H), 3.21 (t, J=8 Hz, 2H), 2.00 (dd, J=8, 12 Hz, 2H), 1.45 (m, 2H).

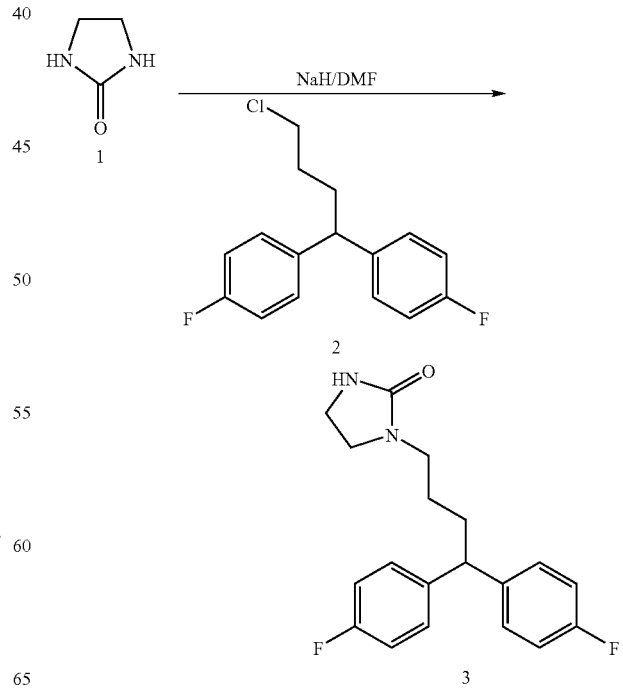

Example 2

1-[4,4-Bis(4-fluorophenyl)butyl]-3-(pyridin-2-ylmethyl)imidazolidin-2-one (5)

To a suspension of sodium hydride (0.06 g, 1.6 mmol) in DMF (1.0 mL) was added a solution of 1-[4,4-bis(4-fluorophenyl)butyl]imidazolidin-2-one (3) (0.2 g, 0.6 mmol) in DMF (1.0 mL) at room temperature. The resulting mixture was stirred at 70° C. for 1.0 hour and cooled to room temperature before adding a solution of compound 4 (0.16 g, 1 mmol, Aldrich) in DMF (0.5 mL). The resulting reaction mixture was stirred at 70° C. for 4 hours. After this period, the mixture was cooled to room temperature and quenched with water (5.0 mL). The mixture was extracted with chloroform (10 mL×2). The organic layer was dried ($Na_2SO_4$) and concentrated to give a crude sample. The crude sample was purified by column chromatography using ethyl acetate/hexane gradient as an eluent to give 65 mg of the title compound 5 as a clear oil. MS: m/z 422. $^1$H NMR (400 MHz, $CDCl_3$): δ 8.56-8.49 (m, 1H), 7.66-7.59 (m, 1H), 7.34-7.26 (m, 2H), 7.22-7.11 (m, 4H), 7.02-6.90 (m, 4H), 4.49 (s, 2H), 3.96-3.88 (m, 1H), 3.33-3.16 (m, 6H), 2.07-1.96 (m, 2H), 1.53-1.44 (m, 2H).

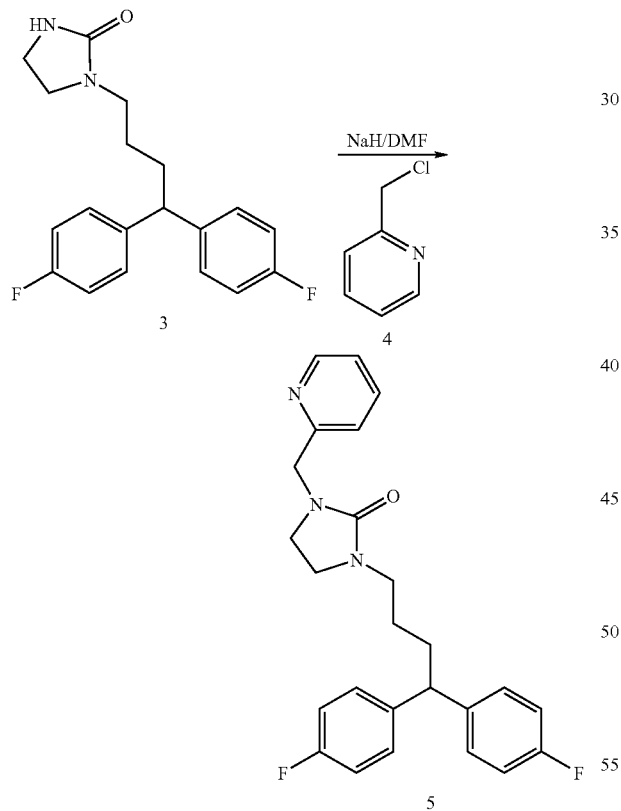

The following compounds were prepared similarly:

1-[4,4-Bis(4-fluorophenyl)butyl]-3-(pyridin-3-ylmethyl) imidazolidin-2-one: $^1$H NMR (400 MHz, $CDCl_3$): δ 8.52 (m, 2H), 7.62 (m, 1H), 7.24 (m, 1H), 7.16 (dd, J=5.2, 8.3 Hz, 4H), 6.96 (m, 4H), 4.37 (s, 2H), 3.92 (t, J=7.9 Hz, 1H), 3.25 (t, J=6.9 Hz, 2H), 3.17 (m, 4H), 2.01 (m, 2H), 1.45 (m, 2H). MS: m/z 422.2 (M+1).

1-[4,4-Bis(4-fluorophenyl)butyl]-3-(pyridin-4-ylmethyl) imidazolidin-2-one: 1H NMR (400 MHz, $CDCl_3$): δ 8.54 (m, 2H), 7.17 (m, 6H), 6.97 (m, 4H), 4.36 (s, 2H), 3.93 (t, J=7.7 Hz, 1H), 3.27 (t, J=7.1 Hz, 2H), 3.20 (m, 4H), 2.02 (m, 2H), 1.45 (m, 2H). MS: m/z 422.2 (M+1).

1-[4,4-Bis(4-fluorophenyl)butyl]-3-[2-(piperidin-1-yl) ethyl]-imidazolidin-2-one: $^1$H NMR (400 MHz, $CDCl_3$): δ 7.16 (m, 4H), 6.96 (m, 4H), 3.90 (t, J=7.9 Hz, 1H), 3.32 (m, 4H), 3.17 (m, 4H), 2.42 (m, 6H), 1.99 (m, 2H), 1.54 (m, 4H), 1.42 (m, 4H). MS: m/z 442.4 (M+1).

Example 3

2-[4,4-Bis(4-fluorophenyl)butyl]-4-benzyloxycarbonyl-2,4-diaza-bicyclo[3.1.0]hexan-3-one (8) 2-[4,4-Bis(4-fluorophenyl)butyl]-2,4-diaza-bicyclo[3.1.0] hexan-3-one (9)

3-Oxo-2,4-diaza-bicyclo[3.1.0]hexane-2-carboxylic acid benzyl ester (6) (0.78 g, 3.34 mmol, Rare Chemicals GmbH) was dissolved in DMF (10.0 mL). Potassium hydroxide (0.28 g, 5.0 mmol) was added to the solution followed by compound 7 (1.37 g, 3.67 mmol). The resulting mixture was stirred at room temperature for 5 hours. Then the mixture was diluted with water (10.0 mL) and extracted with methylene chloride (50 mL×3). The organic layer was dried with anhydrous $Na_2SO_4$ and concentrated to give a crude sample. The crude sample was purified by column chromatography using ethyl acetate/methylene chloride gradient as an eluent to give 1.13 g of the title compound 8 and 90 mg of the title compound 9. MS for compound 8: m/z 477. MS for compound 9: m/z 343.

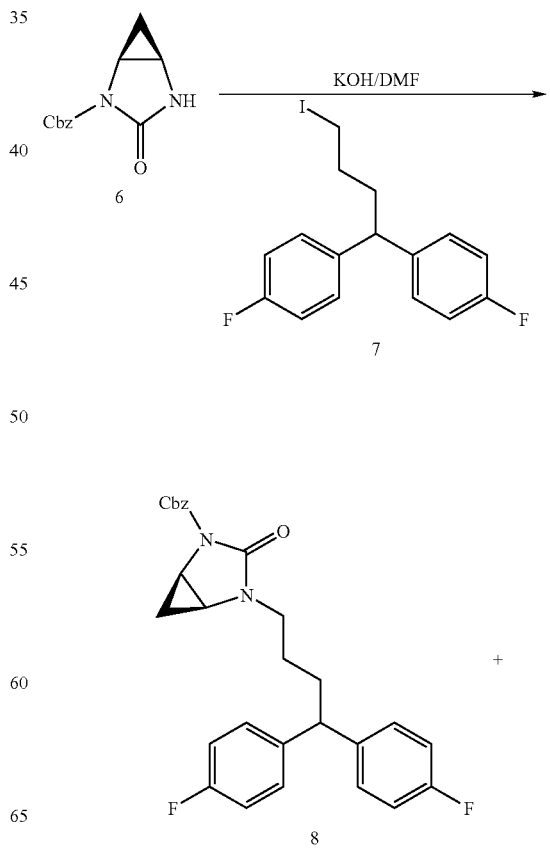

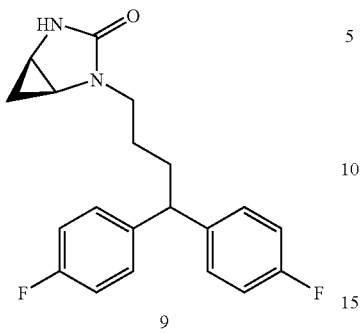

Example 4

2-[4,4-Bis(4-fluorophenyl)butyl]-4-(pyridin-2-yl)methyl-2,4-diaza-bicyclo[3.1.0]hexan-3-one (10)

2-[4,4-Bis(4-fluorophenyl)butyl]-2,4-diaza-bicyclo[3.1.0]hexan-3-one (9) (90 mg, 0.263 mmol) was dissolved in DMF (3.0 mL). Sodium hydride (11 mg, 0.39 mmol) was added to the solution followed by compound 4 (48 mg, 0.26 mmol). The resulting mixture was stirred at room temperature for 15 hours. Then the mixture was diluted with water (1.0 mL) and extracted with methylene chloride (5 mL×3). The organic layer was dried with anhydrous $Na_2SO_4$ and concentrated to give a crude sample. The crude sample was purified by column chromatography using ethyl acetate/methylene chloride gradient as an eluent to give 20 mg of the title compound 10 as clear oil. MS: m/z 434. $^1$H NMR (CDCl$_3$): δ 8.58-8.52 (m, 1H), 7.67-7.61 (m, 1H), 7.35-7.25 (m, 5H), 7.04-6.93 (m, 4H), 4.69-4.62 (m, 1H), 4.53-4.43 (m, 1H), 3.99-3.86 (m, 1H), 3.37-3.27 (m, 2H), 3.14-3.04 (m, 1H), 2.99-2.90 (m, 1H), 2.11-1.95 (m, 2H), 1.59-1.48 (m, 2H), 1.28-1.23 (m, 1H), 0.50-0.42 (m, 1H).

Similarly, 2-[4,4-bis(4-fluorophenyl)butyl]-4-methyl-2,4-diaza-bicyclo[3.1.0]hexan-3-one was prepared. $^1$H NMR (CDCl$_3$): δ 7.16 (m, 4H), 6.96 (m, 4H), 3.91 (t, J=8 Hz, 1H), 3.24 (m, 2H), 3.00 (m, 1H), 2.92 (m, 1H), 2.85 (s, 3H), 2.01 (m, 2H), 1.52 (m, 2H), 1.25 (s, 1H), 0.45 (dd, J=5.7, 11.8 Hz, 1H). MS: m/z 357.1 (M+1).

Example 5

1-[4,4-Bis(4-fluorophenyl)butyl]-1,3-dihydro-benzoimidazol-2-one (12)

To a suspension of sodium hydride (0.72 g, 18 mmol) in DMF (15.0 mL) was added a solution of 1,3-dihydro-benzoimidazol-2-one (11) (2.6 g, 20.0 mmol, Aldrich) in DMF (10.0 mL) at room temperature. The resulting mixture was stirred at room temperature for 30 minutes and a solution of compound 2 (2.8 g, 10 mmol) in DMF (10.0 mL) was added. The resulting mixture was stirred at 60° C. for 4 hours. After this period, the mixture was cooled to room temperature and quenched with water (20 mL). The mixture was extracted with ethyl acetate (100 mL×3). The organic layer was dried with anhydrous $Na_2SO_4$ and concentrated to give a crude sample. The crude sample was purified by column chromatography using ethyl acetate/hexane gradient as an eluent to give the title compound 12. MS: m/z 379. $^1$H NMR (CDCl$_3$): δ 9.41 (s, 1H), 7.10 (m, 8H), 6.92 (t, J=8 Hz, 4H), 3.93 (m, 3H), 2.07 (m, 2H), 1.73 (m, 2H).

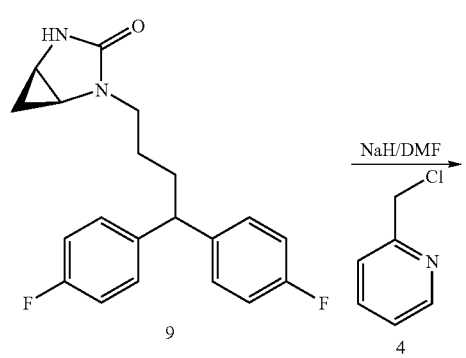

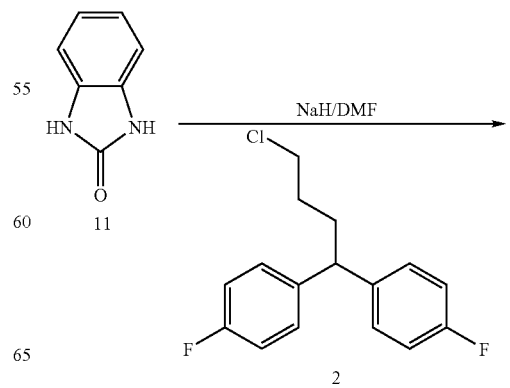

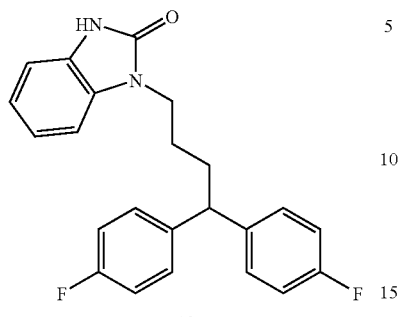

12

Example 6

1-[4,4-Bis(4-fluorophenyl)butyl]-3-(pyridin-2-yl)methyl-1,3-dihydro-benzoimidazol-2-one (13)

To a suspension of sodium hydride (0.06 g, 1.5 mmol) in DMF (1.0 mL) was added a solution of 1-[4,4-bis(4-fluorophenyl)butyl]-1,3-dihydro-benzoimidazol-2-one (12) (0.19 g, 0.5 mmol) in DMF (1.0 mL) at room temperature. The resulting mixture was stirred at 70° C. for 1 hour and cooled to room temperature before adding a solution of compound 4 (0.16 g, 1 mmol, Aldrich) in DMF (0.5 mL). The resulting mixture was stirred at 70° C. for 4 hours. After this period, the mixture was cooled to room temperature and quenched with water (5.0 mL). The mixture was extracted with chloroform (10 mL×2). The organic layer was dried ($Na_2SO_4$) and concentrated to give a crude sample. The crude sample was purified by column chromatography using ethyl acetate/hexane gradient as an eluent to give 65 mg of the title compound 13 as clear oil. MS: m/z 469. $^1$H NMR (CDCl$_3$): δ 8.64 (s, 1H), 8.53 (s, 1H), 7.64-7.56 (m, 1H), 7.23-7.16 (m, 1H), 7.16-7.08 (m, 4H), 7.08-6.98 (m, 2H), 6.98-6.90 (m, 4H), 6.90-6.84 (m, 2H), 5.08 (s, 2H), 4.00-3.87 (m, 3H), 2.11-1.99 (m, 2H), 1.79-1.66 (m, 2H).

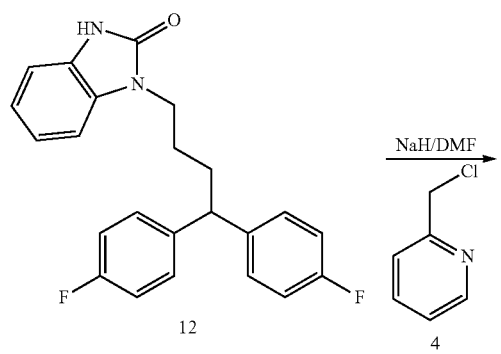

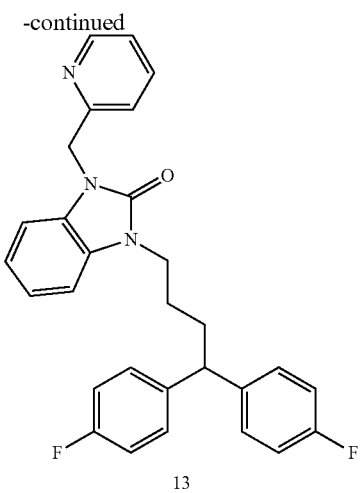

13

Similarly, the following compounds were prepared:

1-[4,4-Bis(4-fluorophenyl)butyl]-3-[2-(piperidin-1-yl)ethyl]-1,3-dihydro-benzoimidazol-2-one: $^1$H NMR (CDCl$_3$): δ 7.12 (dd, J=5.3, 8.8 Hz, 4H), 7.05 (m, 3H), 6.93 (m, 4H), 6.84 (m, 1H), 4.00 (dd, J=8.0, 14.4 Hz, 2H), 3.90 (m, 3H), 2.62 (m, 2H), 2.46 (m, 4H), 2.04 (dd, J=7.6, 15.0 Hz, 2H), 1.70 (m, 2H), 1.54 (m, 4H), 1.41 (m, 2H). MS: m/z 490.4 (M+1);

1-[4,4-Bis(4-fluorophenyl)butyl]-3-(pyridin-3-yl)methyl-1,3-dihydro-benzoimidazol-2-one: $^1$H NMR (CDCl$_3$): δ 8.64 (br s, 1H), 8.53 (br s, 1H), 7.60 (d, J=7.7 Hz, 1H), 7.20 (dd, J=4.9, 7.7 Hz, 1H), 7.13 (dd. J=5.3, 8.6 Hz, 4H), 7.03 (m, 2H), 6.94 (m, 4H), 6.88 (m, 2H), 5.08 (s, 2H), 3.94 (m, 3H), 2.05 (m, 2H), 1.73 (m, 2H). MS: m/z 470.2 (M+1);

1-[4,4-Bis(4-fluorophenyl)butyl]-3-(pyridin-4-yl)methyl-1,3-dihydro-benzoimidazol-2-one: $^1$H NMR (CDCl$_3$): δ 8.52 (br s, 2H), 7.14 (m, 6H), 7.04 (m, 2H), 6.94 (m, 5H), 6.79 (m, 1H), 5.06 (s, 2H), 3.95 (m, 3H), 2.05 (m, 2H), 1.75 (m, 2H). MS: m/z 470.1 (M+1); and 1-[4,4-Bis(4-fluorophenyl)butyl]-3-(pyridin-4-yl)-1,3-dihydro-benzoimidazol-2-one: $^1$H NMR (CDCl$_3$): δ 8.76 (m, 2H), 7.61 (dd, J=1.4, 4.6 Hz, 2H), 7.28 (m, 2H), 7.14 (m, 5H), 6.95 (m, 5H), 3.96 (t, J=7.2 Hz, 1H), 3.94 (m, 2H), 2.10 (m, 2H), 1.77 (m, 2H). MS: m/z 456.1 (M+1).

Example 7

Compounds of the invention described exhibit an IC$_{50}$ value of from about 0.34 μM to about 5 μM when tested in the calcium mobilization and/or electrophysiological assay for N-type calcium channel blocking activity. Some compounds described have been tested in the calcium mobilization assay for L-type calcium channel blocking activity and they exhibit an IC$_{50}$ value of from about 0.20 μM to about >20 μM. Representative values are presented in TABLE 2.

TABLE 2

Evaluation of the tested compounds as N-type calcium channel (NTCC) blockers and L-type calcium channel (LTCC) blockers after a calcium mobilization in vitro assay

| COMPOUND | NTCC IC$_{50}$ (μM) | LTCC IC$_{50}$ (μM) |
| --- | --- | --- |
| 1-(3,3-diphenylpropyl)-3-phenylimidazolidin-2-one | 4.33 | 10~20 |

TABLE 2-continued

Evaluation of the tested compounds as N-type calcium channel (NTCC) blockers and L-type calcium channel (LTCC) blockers after a calcium mobilization in vitro assay

| COMPOUND | NTCC IC$_{50}$ (μM) | LTCC IC$_{50}$ (μM) |
|---|---|---|
| 1-[4,4-bis(4-fluorophenyl)butyl]-imidazolidin-2-one | 3.69 | |
| 1-[4,4-bis(4-fluorophenyl)butyl]-3-(pyridin-4-ylmethyl)imidazolidin-2-one | 1.19 | 3.43 |
| 1-[4,4-bis(4-fluorophenyl)butyl]-3-(3-phenylprop-2-enyl)imidazolidin-2-one | 1.14 | 3.63 |
| 1-[4,4-bis(4-fluorophenyl)butyl]-3-methylimidazolidin-2-one | 0.67 | 0.79 |
| 1-[4,4-bis(4-fluorophenyl)butyl]-3-cyclopropylimidazolidin-2-one | 0.62 | 0.41 |
| 1-[4,4-bis(4-fluorophenyl)butyl]-3-[2-(pyrrolidin-1-yl)ethyl]imidazolidin-2-one | 1.36 | 3.56 |
| 2-[4,4-bis(4-fluorophenyl)butyl]-4-benzyloxycarbonyl-2,4-diazabicyclo[3.1.0]hexan-3-one | 0.34 | 3.29 |
| 1-[4,4-bis(4-fluorophenyl)butyl]-3-[2-(piperidin-1-yl)ethyl]-1,3-dihydro-benzoimidazol-2-one | 2.15 | >20 |
| 1-[4,4-bis(4-fluorophenyl)butyl]-3-(pyridin-2-yl)methyl-1,3-dihydro-benzoimidazol-2-one | 0.81 | 4.69 |

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

The invention claimed is:

1. A compound of Formula I:

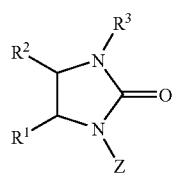

I or a pharmaceutically acceptable salt or prodrug thereof, wherein:

Z is $Z^1$, wherein

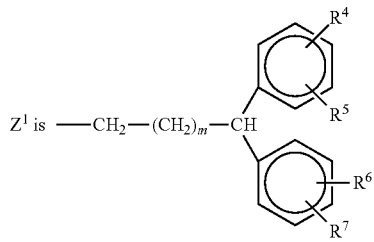

$R^1$ and $R^2$ are both hydrogen or $R^1$ and $R^2$, together with the carbon atoms to which they are attached, form a fused cyclopropyl ring;

$R^3$ is selected from the group consisting of (i) hydrogen;

(ii) alkyl;

(iii) $C_{3-6}$ cycloalkyl;

(iv) —$(CH_2)_p$—Y;

(v)

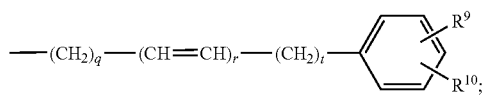

(vi)

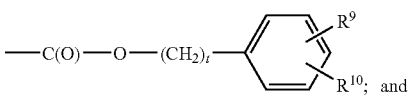
and (vii)

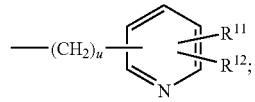

$R^4$, $R^5$, $R^6$, and $R^7$ are each independently selected from the group consisting of hydrogen, alkyl, alkoxy, halogen, haloalkyl, haloalkoxy, hydroxy, hydroxyalkyl, cyano, amino, aminoalkyl, alkylamino, and dialkylamino;

$R^9$ and $R^{10}$ are each independently selected from the group consisting of hydrogen, halogen, alkyl, alkoxy, haloalkyl, haloalkoxy, cyano, hydroxy, and hydroxyalkyl;

$R^{11}$ and $R^{12}$ are each independently selected from the group consisting of hydrogen, halogen, alkyl, alkoxy, haloalkyl, haloalkoxy, cyano, hydroxy, and hydroxyalkyl;

wherein Y is a 3-7 membered saturated heterocyclic ring optionally substituted with one or two substituents independently selected from the group consisting of alkyl, alkoxy, halogen, haloalkyl, haloalkoxy, cyano, hydroxy, and hydroxyalkyl;

m is 0, 1, 2, 3, 4, or 5;

p is 0, 1, 2, 3, or 4;

q and s are each independently 0, 1, 2, 3, 4, or 5;

r is 0 or 1;

t is 1, 2, 3, or 4; and u is 0, 1, 2, 3, or 4.

2. The compound of claim 1, wherein the compound is of Formula V:

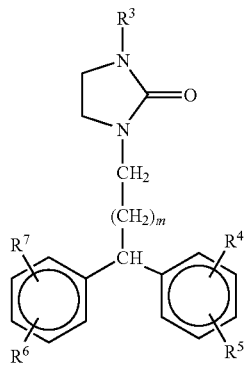

or a pharmaceutically acceptable salt or prodrug thereof, wherein $R^3$-$R^9$ and m are as defined in claim 1.

3. The compound of claim 1, wherein $R^3$ is selected from the group consisting of (i) hydrogen, (ii) alkyl, and (iii) $C_{3-6}$ cycloalkyl.

4. The compound of claim 1, wherein $R^4$, $R^5$, $R^6$ and $R^7$ are each independently selected from the group consisting of hydrogen, alkyl, alkoxy, halogen, haloalkyl, haloalkoxy, hydroxy, cyano, amino, alkylamino, and dialkylamino.

5. The compound of claim 2, which is:
1-(3,3-diphenylpropyl)-3-phenylimidazolidin-2-one;
1-[4,4-bis(4-fluorophenyl)butyl]-3-phenylimidazolidin-2-one;
1-[4,4-bis(4-fluorophenyl)butyl]-3-(3-phenylprop-2-enyl)imidazolidin-2-one;
1-[4,4-bis(4-fluorophenyl)butyl]-3-(pyridin-3-ylmethyl)imidazolidin-2-one;
1-[4,4-bis(4-fluorophenyl)butyl]-3-(pyridin-4-ylmethyl)imidazolidin-2-one;
1-[4,4-bis(4-fluorophenyl)butyl]-3-(pyridin-2-ylmethyl)imidazolidin-2-one;
1-[4,4-bis(4-fluorophenyl)butyl]-3-methylimidazolidin-2-one;
1-[4,4-bis(4-fluorophenyl)butyl]-3-cyclopropylimidazolidin-2-one;
1-[4,4-bis(4-fluorophenyl)butyl]-3-[2-(pyrrolidin-1-yl)ethyl]imidazolidin-2-one;
1-[4,4-bis(4-fluorophenyl)butyl]-3-[2-(piperidin-1-yl)-ethyl]imidazolidin-2-one;
or
1-[4,4-bis(4-fluorophenyl)butyl]-imidazolidin-2-one;
or a pharmaceutically acceptable salt or prodrug thereof.

6. The compound of claim 1, wherein said compound has an $IC_{50}$ of about 100 μM or less for N-type calcium channel blocking activity in a calcium mobilization and/or electrophysiological assay.

7. A pharmaceutical composition, comprising the compound as claimed in claim 1, or a pharmaceutically acceptable salt or prodrug thereof, and a pharmaceutically acceptable carrier.

8. A method of treating, or ameliorating stroke, head trauma, epilepsy, pain, migraine, a mood disorder, schizophrenia, depression, anxiety, a psychosis, hypertension, or cardiac arrhythmia in a mammal, comprising administering an effective amount of a compound of Formula I:

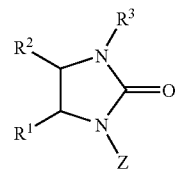

or a pharmaceutically acceptable salt or prodrug thereof, wherein:
Z is $Z^1$, wherein

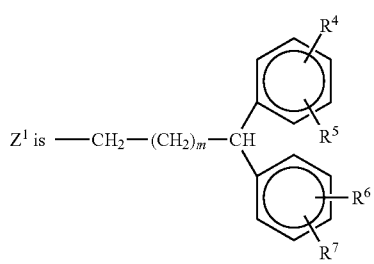

$Z^1$ is 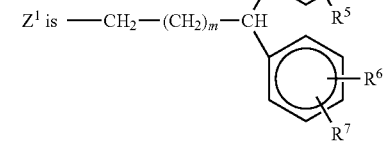

$R^1$ and $R^2$ are both hydrogen or $R^1$ and $R^2$, together with the carbon atoms to which they are attached, form a fused cyclopropyl ring;
$R^3$ is selected from the group consisting of
(i) hydrogen;
(ii) alkyl;
(iii) $C_{3-6}$ cycloalkyl;
(iv) —$(CH_2)_p$—Y;

(v)

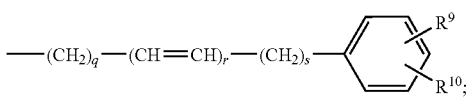

(vi)

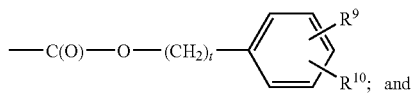

(vii)

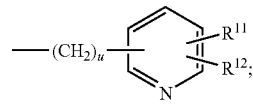

$R^4$, $R^5$, $R^6$, and $R^7$ are each independently selected from the group consisting of hydrogen, alkyl, alkoxy, halogen, haloalkyl, haloalkoxy, hydroxy, hydroxyalkyl, cyano, amino, aminoalkyl, alkylamino, and dialkylamino;
$R^9$ and $R^{10}$ are each independently selected from the group consisting of hydrogen, halogen, alkyl, alkoxy, haloalkyl, haloalkoxy, cyano, hydroxy, and hydroxyalkyl;
$R^{11}$ and $R^{12}$ are each independently selected from the group consisting of hydrogen, halogen, alkyl, alkoxy, haloalkyl, haloalkoxy, cyano, hydroxy, and hydroxyalkyl;
wherein Y is a 3-7 membered saturated heterocyclic ring optionally substituted with one or two substituents independently selected from the group consisting of alkyl, alkoxy, halogen, haloalkyl, haloalkoxy, cyano, hydroxy, and hydroxyalkyl;

m is 0, 1, 2, 3, 4, or 5;

p is 0, 1, 2, 3, or 4;

q and s are each independently 0, 1, 2, 3, 4, or 5;

r is 0 or 1;

t is 0, 1, 2, 3, or 4; and u is 0, 1, 2, 3, or 4;

to a mammal in need of such treatment or amelioration.

9. The method of claim 8, wherein the method is of treating or ameliorating pain.

10. A method of blocking calcium channels in a mammal, comprising administering to the mammal at least one compound of Formula I:

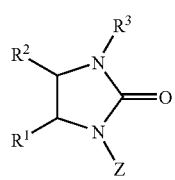

I or a pharmaceutically acceptable salt or prodrug thereof, wherein:

Z is $Z^1$, wherein

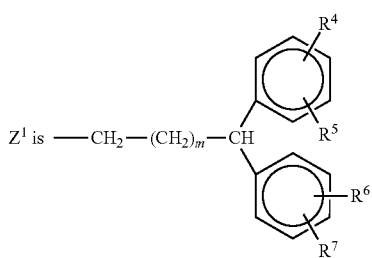

$R^1$ and $R^2$ are both hydrogen or $R^1$ and $R^2$, together with the carbon atoms to which they are attached, form a fused cyclopropyl ring;

$R^3$ is selected from the group consisting of (i) hydrogen;

(ii) alkyl;

(iii) $C_{3-6}$ cycloalkyl;

(iv) —$(CH_2)_p$—Y;

(v)

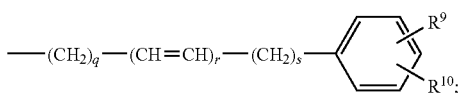

(vi)

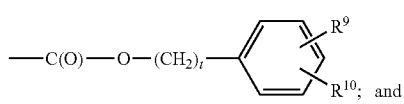

(vii)

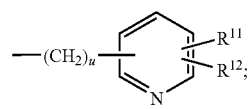

$R^4$, $R^5$, $R^6$, and $R^7$ are each independently selected from the group consisting of hydrogen, alkyl, alkoxy, halogen, haloalkyl, haloalkoxy, hydroxy, hydroxyalkyl, cyano, amino, aminoalkyl, alkylamino, and dialkylamino;

$R^9$ and $R^{10}$ are each independently selected from the group consisting of hydrogen, halogen, alkyl, alkoxy, haloalkyl, haloalkoxy, cyano, hydroxy, and hydroxyalkyl;

$R^{11}$ and $R^{12}$ are each independently selected from the group consisting of hydrogen, halogen, alkyl, alkoxy, haloalkyl, haloalkoxy, cyano, hydroxy, and hydroxyalkyl;

wherein Y is a 3-7 membered saturated heterocyclic ring optionally substituted with one or two substituents independently selected from the group consisting of alkyl, alkoxy, halogen, haloalkyl, haloalkoxy, cyano, hydroxy, and hydroxyalkyl;

m is 0, 1, 2, 3, 4, or 5;

p is 0, 1, 2, 3, or 4;

q and s are each independently 0, 1, 2, 3, 4, or 5;

r is 0 or 1;

t is 0, 1, 2, 3, or 4; and u is 0, 1, 2, 3, or 4.

11. A compound of Formula I as claimed in claim 1, or a pharmaceutically acceptable salt or prodrug thereof, wherein the compound is $^3$H or $^{14}$C radiolabeled.

12. A method for screening a candidate compound for the ability to bind to a receptor using a radiolabeled compound of claim 11, comprising:

a) introducing a fixed concentration of the radiolabeled compound to the receptor to form a mixture;

b) titrating the mixture with the candidate compound; and c) determining the binding of the candidate compound to said receptor.

13. The compound of claim 4, wherein $R^4$ and $R^6$ are both hydrogen and $R^5$ and $R^7$ are each independently selected from the group consisting of hydrogen, alkyl, alkoxy, halogen, haloalkyl, haloalkoxy, hydroxy, cyano, amino, alkylamino, and dialkylamino.

14. The method of claim 9, wherein said pain is acute pain, chronic pain or surgical pain.

15. The method of claim 14, wherein said pain is chronic pain.

16. The method of claim 10, wherein N-type calcium channels are blocked.

17. The compound of claim 1, wherein the compound is of Formula VI:

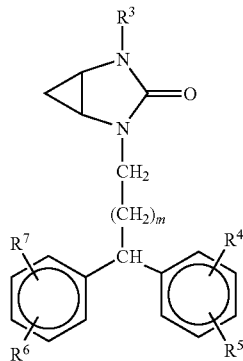

or a pharmaceutically acceptable salt or prodrug thereof, wherein $R^3$-$R^7$ and m are as defined in claim 1.

18. The compound of claim 1, wherein $R^3$ is —$(CH_2)_p$—Y, wherein Y is a 3-7 membered saturated heterocyclic ring optionally substituted with one or two substituents independently selected from the group consisting of alkyl, alkoxy, halogen, haloalkyl, haloalkoxy, cyano, hydroxy, and hydroxyalkyl, and p is 0, 1, 2, 3, or 4.

19. The compound of claim 1, wherein $R^3$ is

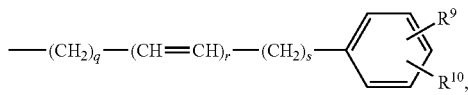

wherein $R^9$ and $R^{10}$ are each independently selected from the group consisting of hydrogen, halogen, alkyl, alkoxy, haloalkyl, haloalkoxy, cyano, hydroxy, and hydroxyalkyl, r is 0 or 1, and q and s are each independently 0, 1, 2, 3, 4, or 5.

20. The compound of claim 1, wherein $R^3$ is

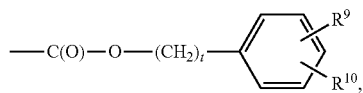

wherein $R^9$ and $R^{10}$ are each independently selected from the group consisting of hydrogen, halogen, alkyl, alkoxy, haloalkyl, haloalkoxy, cyano, hydroxy, and hydroxyalkyl, and t is 0, 1, 2, 3, or 4.

21. The compound of claim 1, wherein $R^3$ is

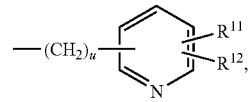

wherein $R^{11}$ and $R^{12}$ are each independently selected from the group consisting of hydrogen, halogen, alkyl, alkoxy, haloalkyl, haloalkoxy, cyano, hydroxy, and hydroxyalkyl, and u is 0, 1, 2, 3, or 4.

22. The compound of claim 17, which is:
2-[4,4-bis(4-fluorophenyl)butyl]-4-methyl-2,4-diazabicyclo[3.1.0]hexan-3-one;
2-[4,4-bis(4-fluorophenyl)butyl]-4-(pyridin-2-yl)methyl-2,4-diazabicyclo[3.1.0]hexan-3-one;
2-[4,4-bis(4-fluorophenyl)butyl]-4-benzyloxycarbonyl-2,4-diazabicyclo[3.1.0]hexan-3-one; or
2-[4,4-bis(4-fluorophenyl)butyl]-2,4-diaza-bicyclo[3.1.0]hexan-3-one;
or a pharmaceutically acceptable salt or prodrug thereof.

23. A compound, which is:
1-[4,4-bis(4-fluorophenyl)butyl]-3-[2-(piperidin-1-yl)ethyl]-1,3-dihydro-benzohnidazol-2-one;
1-[4,4-bis(4-fluorophenyl)butyl]-3-(pyridine-3yl)methyl-1,3dihydro-benzoimidazol -2-one;
1-[4-bis(4-fluorophenyl)butyl]-3-(pyridin-4-yl)methyl-1,3-dihydro-benzoimidazol-2-one
1-[4-bis(4-fluorophenyl)butyl]-3-(pyridin-2-yl)methyl-1,3-dihydro-benzoimidazol-2-one;
1-[4-bis(4-fluorophenyl)butyl]-3-(pyridin-4-yl)- 1,3-dihydro-benzoimidazol-2-one; or
1-[4,4-bis(4-fluorophenyl)butyl]- 1,3-dihydro-benzoimidazol-2-one;
or a pharmaceutically acceptable salt or prodrug thereof.

24. A pharmaceutical composition, comprising the compound as claimed in claim 23, or a pharmaceutically acceptable salt or prodrug thereof, and a pharmaceutically acceptable carrier.

* * * * *